United States Patent
Inoue et al.

(10) Patent No.: US 9,155,158 B2
(45) Date of Patent: Oct. 6, 2015

(54) ORGANOMETALLIC COMPLEX, LIGHT-EMITTING ELEMENT, DISPLAY DEVICE, ELECTRONIC DEVICE, AND LIGHTING DEVICE

(75) Inventors: Hideko Inoue, Kanagawa (JP); Yui Yamada, Kanagawa (JP); Nobuharu Ohsawa, Tochigi (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 520 days.

(21) Appl. No.: 13/432,253

(22) Filed: Mar. 28, 2012

(65) Prior Publication Data
US 2012/0248969 A1    Oct. 4, 2012

(30) Foreign Application Priority Data

Apr. 1, 2011    (JP) .................................. 2011-081583

(51) Int. Cl.
| | | |
|---|---|---|
| H01L 51/54 | (2006.01) | |
| C09K 11/06 | (2006.01) | |
| H05B 33/14 | (2006.01) | |
| C07F 15/00 | (2006.01) | |
| H01L 51/00 | (2006.01) | |
| H01L 51/50 | (2006.01) | |

(52) U.S. Cl.
CPC ............ *H05B 33/14* (2013.01); *C07F 15/0033* (2013.01); *C09K 11/06* (2013.01); *H01L 51/0085* (2013.01); *C09K 2211/1007* (2013.01); *C09K 2211/1059* (2013.01); *C09K 2211/185* (2013.01); *H01L 51/0072* (2013.01); *H01L 51/0074* (2013.01); *H01L 51/0087* (2013.01); *H01L 51/504* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,915,415 | B2 | 3/2011 | Knowles et al. |
| 8,142,909 | B2 | 3/2012 | Beers et al. |
| 8,580,397 | B2 | 11/2013 | Omary |
| 8,795,851 | B2 | 8/2014 | Inoue et al. |
| 2004/0124766 | A1 | 7/2004 | Nakagawa et al. |
| 2005/0003233 | A1 | 1/2005 | Igarashi et al. |
| 2007/0085073 | A1 | 4/2007 | Inoue et al. |
| 2011/0101854 | A1 | 5/2011 | Inoue et al. |
| 2011/0220882 | A1* | 9/2011 | Inoue et al. ............ 257/40 |
| 2011/0260145 | A1 | 10/2011 | Omary |
| 2012/0133273 | A1 | 5/2012 | Inoue et al. |

FOREIGN PATENT DOCUMENTS

| | | |
|---|---|---|
| EP | 1 777 229 A1 | 4/2007 |
| JP | 2006-060198 A | 3/2006 |
| JP | 2007-137872 | 6/2007 |
| JP | 2007-208102 | 8/2007 |
| JP | 2008-69221 | 3/2008 |
| JP | 2008-074921 A | 4/2008 |
| JP | 2009-001742 A | 1/2009 |
| WO | WO 2009/107497 A1 | 9/2009 |

OTHER PUBLICATIONS

International Search Report re application No. PCT/JP2010/068796, dated Nov. 30, 2010.
Written Opinion re application No. PCT/JP2010/068796, dated Nov. 30, 2010.

* cited by examiner

*Primary Examiner* — Marie R. Yamnitzky
(74) *Attorney, Agent, or Firm* — Husch Blackwell LLP

(57) ABSTRACT

The organometallic complex, which is a novel substance, is represented by General Formula (G1) or General Formula (G2). In General Formula (G1), $R^1$ represents an alkyl group having 1 to 4 carbon atoms and $R^2$ to $R^{10}$ each represents hydrogen or an alkyl group having 1 to 4 carbon atoms. M represents a Group 9 element or a Group 10 element. When M is a Group 9 element, n is 3, and when M is a Group 10 element, N is 2. In General Formula (G2), $R^{11}$ represents an alkyl group having 1 to 4 carbon atoms and $R^{12}$ to $R^{20}$ each represents hydrogen or an alkyl group having 1 to 4 carbon atoms. M represents a Group 9 element or a Group 10 element. When M is a Group 9 element, n is 3, and when M is a Group 10 element, N is 2.

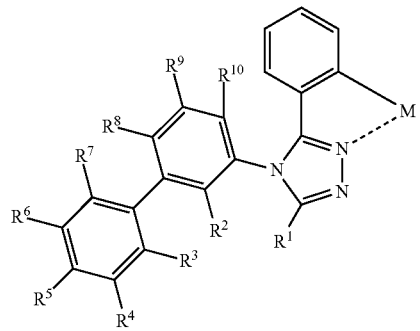

(G1)

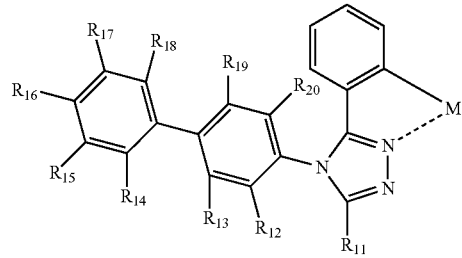

(G2)

22 Claims, 20 Drawing Sheets

ORGANOMETALLIC COMPLEX, LIGHT-EMITTING ELEMENT, DISPLAY DEVICE, ELECTRONIC DEVICE, AND LIGHTING DEVICE

BACKGROUND OF THE INVENTION

1. Field of the Invention

The present invention disclosed in this specification relates to organometallic complexes which can emit light by current excitation. In particular, the present invention relates to organometallic complexes which can emit light from a triplet excited state. The present invention also relates to a light-emitting element, a display device, an electronic device, a light-emitting device, and a lighting device each of which includes any of the organometallic complexes.

2. Description of the Related Art

It has been reported that in a light-emitting element including a layer containing a light-emitting material (light-emitting layer) between a pair of electrodes (anode and cathode), a variety of organic compounds can be used as the light-emitting material.

The light-emitting element is said to have the following light emission mechanism: when voltage is applied between the pair of electrodes with the light-emitting layer interposed therebetween, electrons injected from the cathode and holes injected from the anode are recombined in the light-emitting layer to form molecular excitons, and the molecular excitons release energy to emit light when returning to a ground state. Singlet excitation and triplet excitation are known as excited states, and light emission can be obtained through either of the excited states.

In such a current-excitation light-emitting element, more excitons are generated in a triplet excited state than in a singlet excited state; thus, the emission efficiency of the light-emitting element can be increased by using a material which can emit light from the triplet excited state (phosphorescent material). Therefore, many attempts have been made to use a phosphorescent material as a light-emitting material.

As a typical example of a phosphorescent material emitting green to blue light, a metal complex in which a ligand having a heterocyclic ring skeleton is coordinated to iridium (Ir) that is a central metal is given (e.g., see Patent Document 1). In Patent Document 1, an iridium complex having a triazole derivative as a ligand is disclosed.

REFERENCE

[Patent Document 1] Japanese Published Patent Application No. 2007-137872

SUMMARY OF THE INVENTION

As reported in Patent Document 1, although the development of the phosphorescent material emitting green to blue light has been advanced, there are still only a few substances which have excellent emission efficiency and emit green to blue phosphorescence; therefore, further development of the phosphorescent material is expected.

Embodiments of the present invention are made in view of the above problem. An object of one embodiment of the present invention is to provide a novel substance which has excellent emission efficiency and can emit blue-green to blue phosphorescence. An object of one embodiment of the present invention is to provide a light-emitting element, a light-emitting device, a display device, a lighting device, or an electronic device which contains the novel substance which can emit phosphorescence.

The inventors have found that an orthometalated complex having a 4-biphenyl-3-phenyl4H-1,2,4-triazole derivative as a ligand emits phosphorescence in a wavelength range of green to blue.

In other words, one embodiment of the present invention is an organometallic complex having a structure represented by General Formula (G1) below.

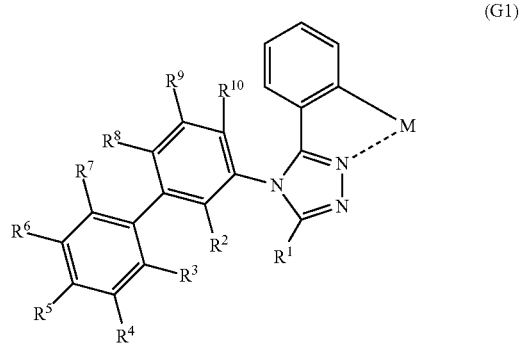

(G1)

In the formula, $R^1$ represents an alkyl group having 1 to 4 carbon atoms and $R^2$ to $R^{10}$ each represents hydrogen or an alkyl group having 1 to 4 carbon atoms. In addition, M represents a Group 9 element or a Group 10 element.

One embodiment of the present invention is an organometallic complex having a structure represented by General Formula (G2) below.

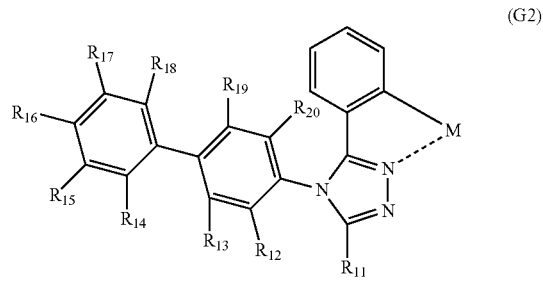

(G2)

In the formula, $R^{11}$ represents an alkyl group having 1 to 4 carbon atoms and $R^{12}$ to $R^{20}$ each represents hydrogen or an alkyl group having 1 to 4 carbon atoms. In addition, M represents a Group 9 element or a Group 10 element.

One embodiment of the present invention is an organometallic complex represented by General Formula (G3) below.

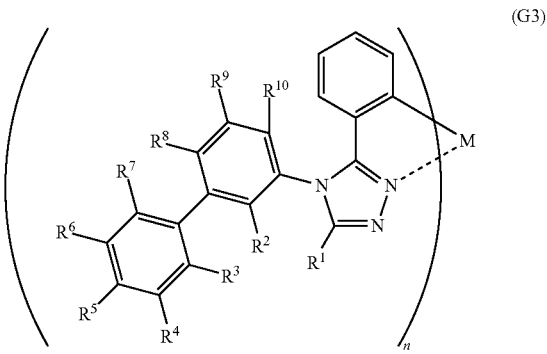

(G3)

In the formula, $R^1$ represents an alkyl group having 1 to 4 carbon atoms and $R^2$ to $R^{10}$ each represents hydrogen or an alkyl group having 1 to 4 carbon atoms. In addition, M represents a Group 9 element or a Group 10 element. In addition, when M is a Group 9 element, n is 3, and when M is a Group 10 element, n is 2.

One embodiment of the present invention is an organometallic complex represented by General Formula (G4) below.

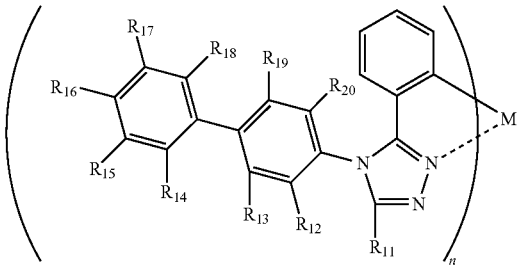

(G4)

In the formula, $R^{11}$ represents an alkyl group having 1 to 4 carbon atoms and $R^{12}$ to $R^{20}$ each represents hydrogen or an alkyl group having 1 to 4 carbon atoms. In addition, M represents a Group 9 element or a Group 10 element. In addition, when M is a Group 9 element, n is 3, and when M is a Group 10 element, n is 2.

One embodiment of the present invention is an organometallic complex represented by General Formula (G5) below.

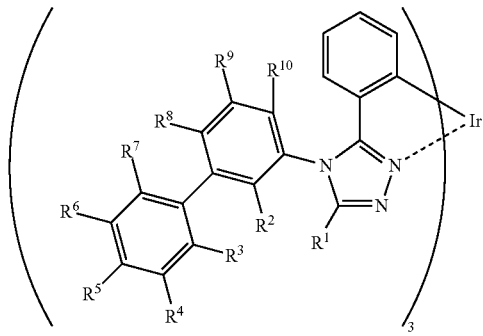

(G5)

In the formula, $R^1$ represents an alkyl group having 1 to 4 carbon atoms and $R^2$ to $R^{10}$ each represents hydrogen or an alkyl group having 1 to 4 carbon atoms.

One embodiment of the present invention is an organometallic complex represented by General Formula (G6) below.

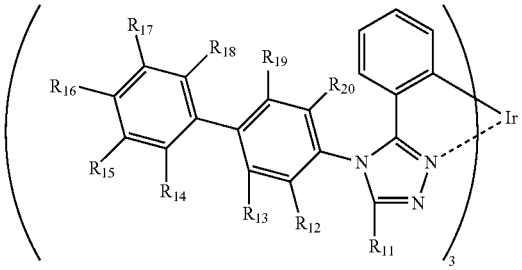

(G6)

In the formula, $R^{11}$ represents an alkyl group having 1 to 4 carbon atoms and $R^{12}$ to $R^{20}$ each represents hydrogen or an alkyl group having 1 to 4 carbon atoms.

Here, specific examples of the alkyl group having 1 to 4 carbon atoms for $R^1$ or $R^{11}$ include a methyl group, an ethyl group, a propyl group, an isopropyl group, a butyl group, a sec-butyl group, an isobutyl group, and a tert-butyl group.

Note that the alkyl group for $R^1$ or $R^{11}$ preferably has greater than or equal to 2 and less than or equal to 4 carbon atoms, particularly greater than or equal to 3 and less than or equal to 4 carbon atoms. In an organometallic complex in which $R^1$ or $R^{11}$ is an alkyl group having greater than or equal to 2 and less than or equal to 4 carbon atoms, intermolecular interaction is suppressed and the sublimation temperature can be lower than that in the case where $R^1$ or $R^{11}$ is hydrogen in spite of a higher molecular weight. As a result, the evaporativity of the organometallic complex can be increased.

Further, the alkyl group for $R^1$ or $R^{11}$ is more preferably a branched alkyl group. A branched alkyl group suppresses an increase in the polarity of the organometallic complex, so that yield after purification by column chromatography can be increased. Further, by introducing a branched alkyl group, the driving voltage of a manufactured light-emitting element including the organometallic complex can be reduced.

Thus, the alkyl group for $R^1$ or $R^{11}$ is more preferably an isopropyl group, an isobutyl group, or a tert-butyl group.

Specific examples of $R^2$ to $R^{10}$ or $R^{12}$ to $R^{20}$ include a methyl group, an ethyl group, a propyl group, an isopropyl group, and a tert-butyl group. Note that $R^2$, $R^7$, $R^{13}$, and $R^{18}$ may be respectively bonded to $R^3$, $R^8$, $R^{14}$, and $R^{19}$ to form a ring and that a methylene group, an ethylene group, and the like can be given as examples of a bivalent group bonded to these. In the case where a methylene group is bonded to these, a biphenyl group bonded to the 4-position of triazole can be regarded as a fluorenyl group.

One embodiment of the present invention is an organometallic complex represented by Structural Formula (1) below.

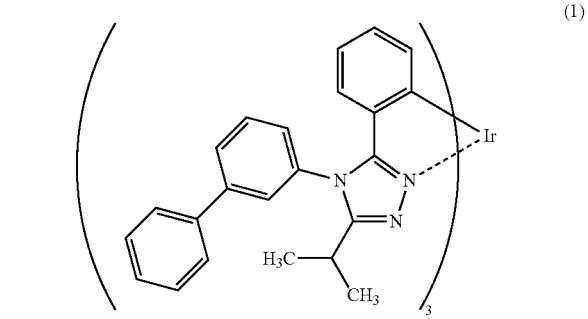

(1)

One embodiment of the present invention is an organometallic complex represented by Structural Formula (2) below.

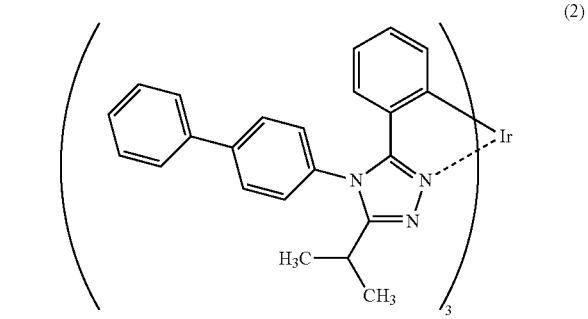

(2)

One embodiment of the present invention is an organometallic complex represented by Structural Formula (3) below.

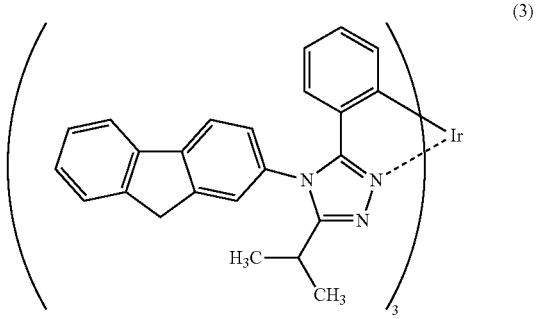

One embodiment of the present invention is a light-emitting element including a layer containing any of the organometallic complexes between a pair of electrodes. The layer containing any of the organometallic complexes may be a light-emitting layer.

One embodiment of the present invention is a light-emitting element including, between a pair of electrodes, a first light-emitting unit containing any of the organometallic complexes and a second light-emitting unit containing a light-emitting material emitting light with a longer wavelength than the organometallic complex.

One embodiment of the present invention is a light-emitting element including, between a pair of electrodes, a first light-emitting unit containing any of the organometallic complexes, a second light-emitting unit containing a first light-emitting material emitting light with a wavelength longer than that emitted from the organometallic complex, and a third light-emitting unit containing a second light-emitting material emitting light with a wavelength longer that that of light emitted from the organometallic complex and shorter than that of light emitted from the first light-emitting material.

One embodiment of the present invention is a display device including any of the light-emitting elements in a pixel portion.

One embodiment of the present invention is an electronic device including the display device in a display portion.

One embodiment of the present invention is a lighting device including any of the light-emitting elements as a light source.

In this specification, a "light-emitting device" means general devices each including a light-emitting element; specifically, the light-emitting device includes, in its category, a backlight used in a display device such as a television or a mobile phone; a traffic light; a light for lighting, such as a street light or illumination on the street; a lighting device; a light for growing seedlings that can be used in a plastic greenhouse; and the like.

In this specification, the expression "A and B are connected" refers to the case where A and B are electrically connected (i.e., A and B are connected with another element or circuit interposed therebetween), the case where A and B are functionally connected (i.e., A and B are functionally connected with another circuit interposed therebetween), or the case where A and B are directly connected (i.e., A and B are connected without another element or circuit interposed therebetween).

According to one embodiment of the present invention, a novel substance which can emit phosphorescence can be provided. According to one embodiment of the present invention, a novel substance which has high emission efficiency can be provided. According to one embodiment of the present invention, a light-emitting element, a light-emitting device, a display device, a lighting device, or an electronic device which contains the novel substance can be provided. According to one embodiment of the present invention, a light-emitting element, a light-emitting device, a display device, a lighting device, or an electronic device which has high emission efficiency can be provided. According to one embodiment of the present invention, a light-emitting element, a light-emitting device, a display device, a lighting device, or an electronic device which has excellent reliability can be provided. According to one embodiment of the present invention, a light-emitting element, a light-emitting device, a display device, a lighting device, or an electronic device which has low power consumption can be provided.

DETAILED DESCRIPTION OF THE INVENTION

Figure 1A:
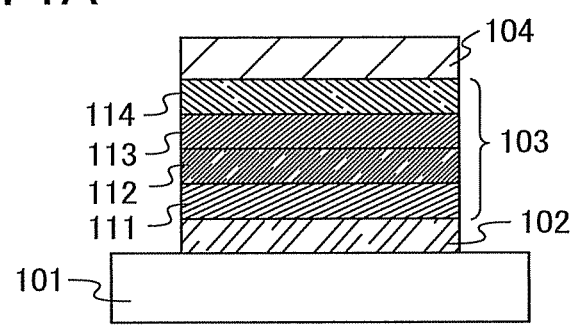
FIGS. 1A and 1B are conceptual diagrams of light-emitting elements according to one embodiment of the present invention.

Embodiments and examples of the present invention will be described in detail with reference to the accompanying drawings. Note that the present invention is not limited to the description below, and it is easily understood by those skilled in the art that modes and details can be modified in various ways without departing from the purpose and scope of the present invention. Therefore, in the embodiments and examples of the present invention described below, reference numerals denoting the same portions are used in common in different drawings.

The embodiments and examples described below can be implemented by being combined with any of the other embodiments and examples described in this specification unless otherwise mentioned.

Embodiment 1

One embodiment of the present invention is an orthometalated complex having a 4-biphenyl-3-phenyl4H-1,2,4-triazole derivative as a ligand. In other words, one embodiment of the present invention described in this embodiment is an organometallic complex having a structure represented by General Formula (G1).

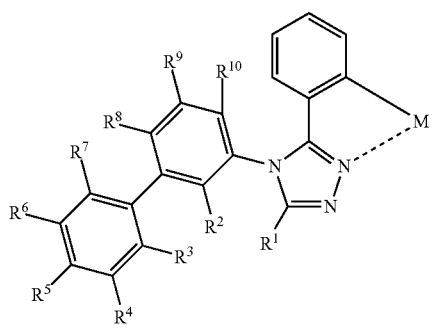

(G1)

In General Formula (G1), $R^1$ represents an alkyl group having 1 to 4 carbon atoms and $R^2$ to $R^{10}$ each represents hydrogen or an alkyl group having 1 to 4 carbon atoms. In addition, M represents a Group 9 element or a Group 10 element.

One embodiment of the present invention described in this embodiment is an organometallic complex having a structure represented by General Formula (G2).

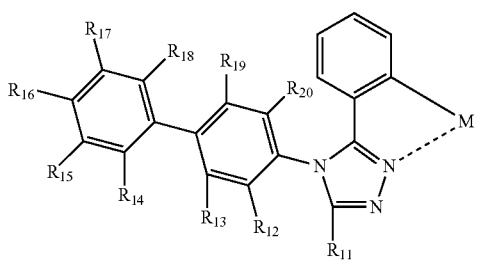

(G2)

In General Formula (G2), $R^{11}$ represents an alkyl group having 1 to 4 carbon atoms and $R^{12}$ to $R^{20}$ each represents hydrogen or an alkyl group having 1 to 4 carbon atoms. In addition, M represents a Group 9 element or a Group 10 element.

The above organometallic complexes having the structures represented by General Formula (G1) and General Formula (G2) can be represented as below.

In other words, one embodiment of the present invention is an organometallic complex represented by General Formula (G3) below.

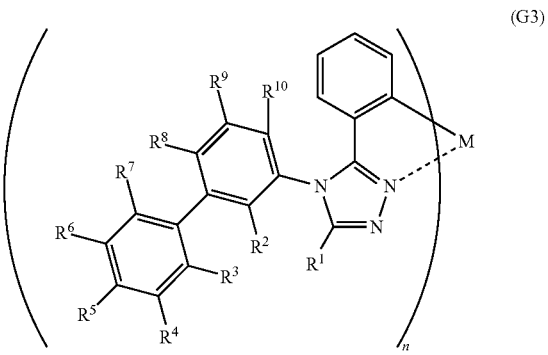

(G3)

In General Formula (G3), $R^1$ represents an alkyl group having 1 to 4 carbon atoms and $R^2$ to $R^{10}$ each represents hydrogen or an alkyl group having 1 to 4 carbon atoms. In addition, M represents a Group 9 element or a Group 10 element. In addition, when M is a Group 9 element, n is 3, and when M is a Group 10 element, n is 2.

One embodiment of the present invention is an organometallic complex represented by General Formula (G4) below.

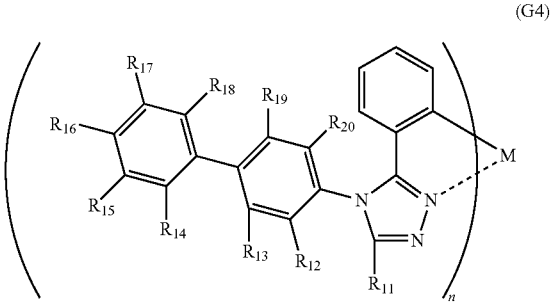

(G4)

In General Formula (G4), $R^{11}$ represents an alkyl group having 1 to 4 carbon atoms and $R^{12}$ to $R^{20}$ each represents hydrogen or an alkyl group having 1 to 4 carbon atoms. In addition, M represents a Group 9 element or a Group 10 element. When M is a Group 9 element, n is 3, and when M is a Group 10 element, n is 2.

In the case where M is iridium in the organometallic complexes represented by the above general formulae, the organometallic complexes have high emission efficiency and are useful. Therefore, the organometallic complexes described in this embodiment are preferably organometallic complexes represented by General Formula (G5) and General Formula (G6) below.

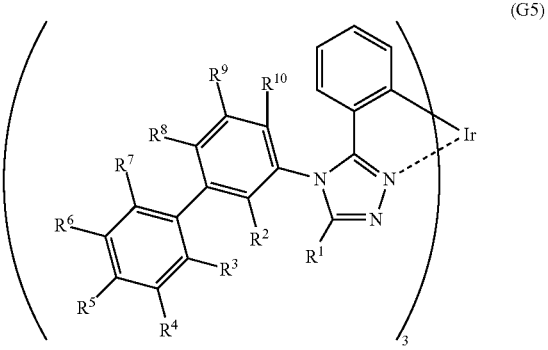

(G5)

In General Formula (G5), $R^1$ represents an alkyl group having 1 to 4 carbon atoms and $R^2$ to $R^{10}$ each represents hydrogen or an alkyl group having 1 to 4 carbon atoms.

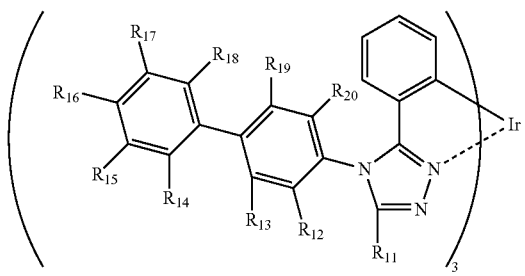

(G6)

In General Formula (G6), $R^{11}$ represents an alkyl group having 1 to 4 carbon atoms and $R^{12}$ to $R^{20}$ each represents hydrogen or an alkyl group having 1 to 4 carbon atoms.

Here, specific examples of the alkyl group having 1 to 4 carbon atoms for $R^1$ or $R^{11}$ include a methyl group, an ethyl group, a propyl group, an isopropyl group, a butyl group, a sec-butyl group, an isobutyl group, and a tert-butyl group.

Note that the alkyl group for $R^1$ or $R^{11}$ preferably has greater than or equal to 2 and less than or equal to 4 carbon atoms, particularly greater than or equal to 3 and less than or equal to 4 carbon atoms. In an organometallic complex in which $R^1$ or $R^{11}$ is an alkyl group having greater than or equal to 2 and less than or equal to 4 carbon atoms, intermolecular interaction is suppressed and the sublimation temperature can be lower than that in the case where $R^1$ or $R^{11}$ is hydrogen in spite of a higher molecular weight. As a result, the evaporativity of the organometallic complex can be increased.

Further, the alkyl group for $R^1$ or $R^{11}$ is more preferably a branched alkyl group. A branched alkyl group suppresses an increase in the polarity of the organometallic complex, so that yield of the organometallic complex after purification by column chromatography can be increased. Further, by introducing the branched alkyl group, the driving voltage of a manufactured light-emitting element including the organometallic complex can be reduced.

Thus, the alkyl group for $R^1$ or $R^{11}$ is more preferably an isopropyl group, an isobutyl group, or a tert-butyl group.

Specific examples of $R^2$ to $R^{10}$ or $R^{12}$ to $R^{20}$ include a methyl group, an ethyl group, a propyl group, an isopropyl group, and a tert-butyl group. Note that $R^2$, $R^7$, $R^{13}$, and $R^{18}$ may be respectively bonded to $R^3$, $R^8$, $R^{14}$, and $R^{19}$ to form a ring and that a methylene group, an ethylene group, and the like can be given as examples of a bivalent group connected to these. In the case where a methylene group is bonded to them, a biphenyl group bonded to the 4-position of triazole can be regarded as a fluorenyl group.

Further, the inventors have found that the purity of blue emission of a manufactured light-emitting element including any of the organometallic complexes can be improved by introducing a biphenyl group to nitrogen at the 4-positions of triazole rings in General Formulae (G5) and (G6). As for particularly the organometallic complex represented by General Formula (G5), the full width at half maximum of an emission spectrum is significantly reduced; thus, a large effect of improving the purity of blue emission can be obtained, and m-biphenyl group is more preferably introduced to nitrogen at the 4-position of the triazole ring. Note that the biphenyl group may have a substituent.

As specific examples of the organometallic complexes having the structures represented by General Formulae (G1) to (G6), organometallic complexes represented by Structural Formulae (100) to (121) can be given. Note that the present invention is not limited to the organometallic complexes represented by these structural formulae.

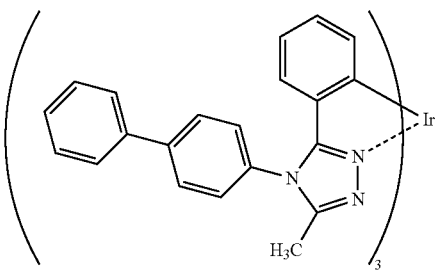

(100)

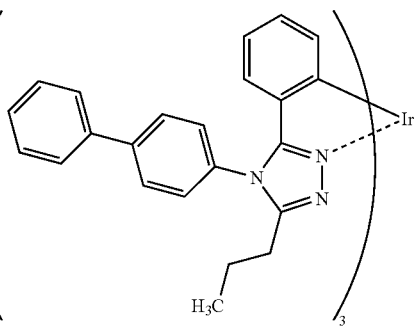

(101)

(102)

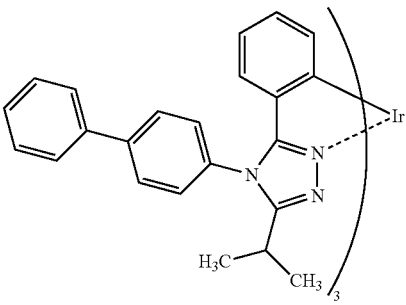

(103)

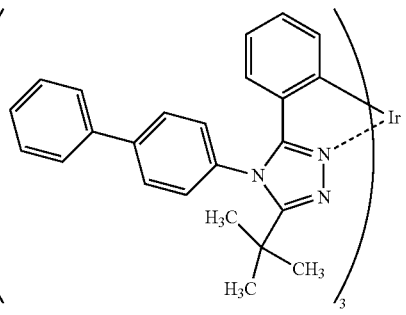

(104)

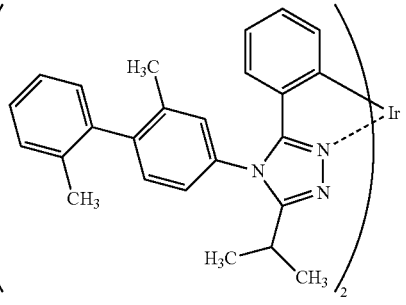

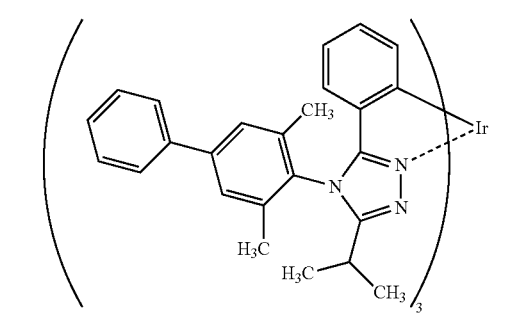 (105)
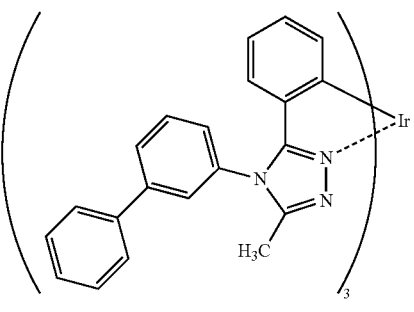 (110)
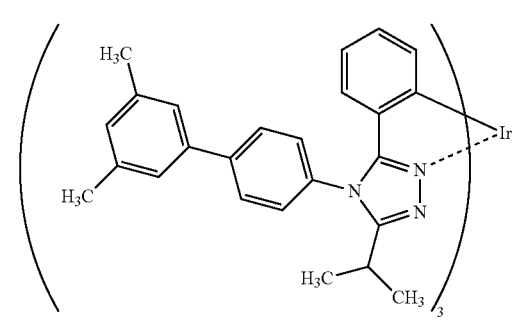 (106)
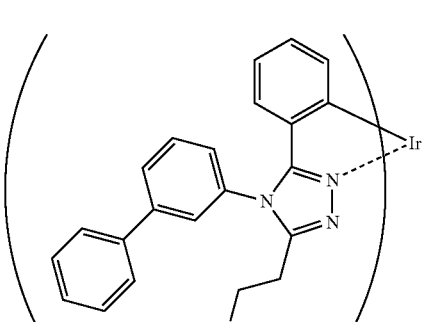 (111)
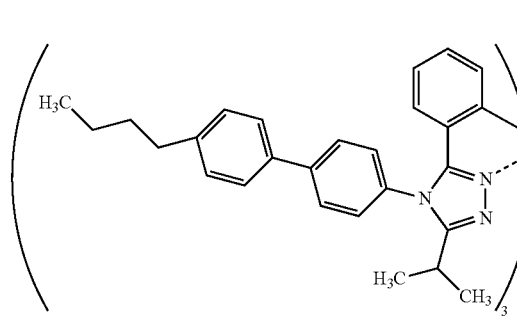 (107)
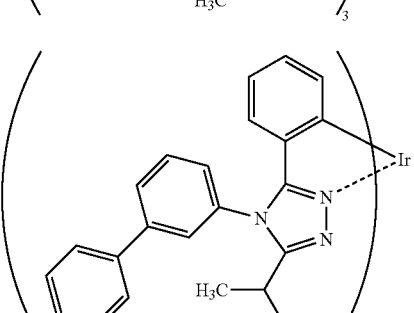 (112)
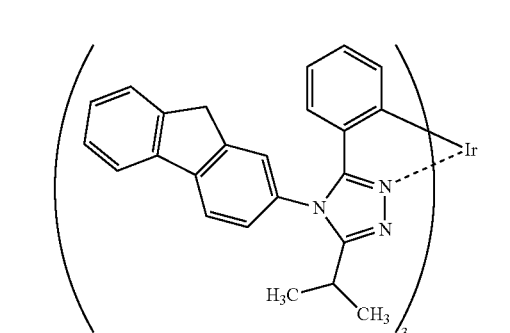 (108)
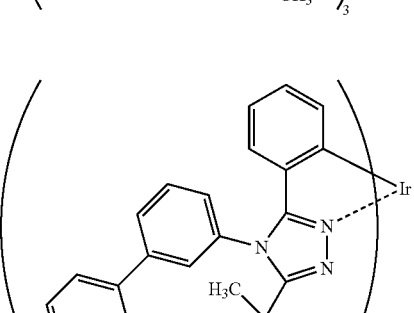 (113)
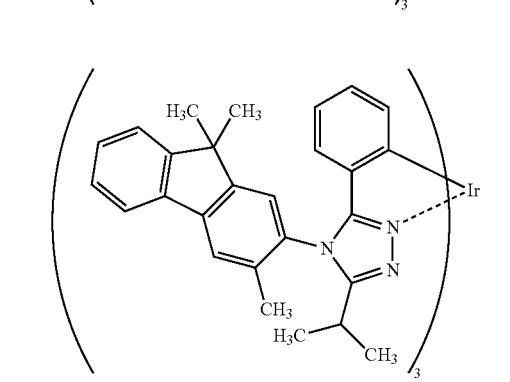 (109)
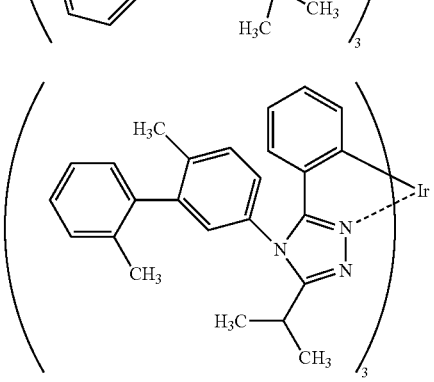 (114)

(115) 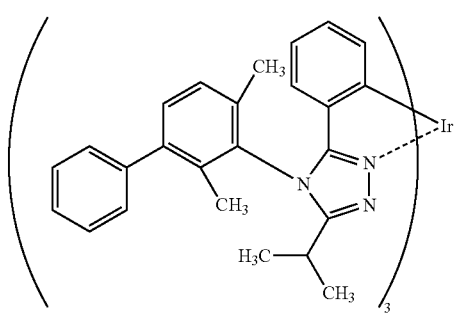

(116) 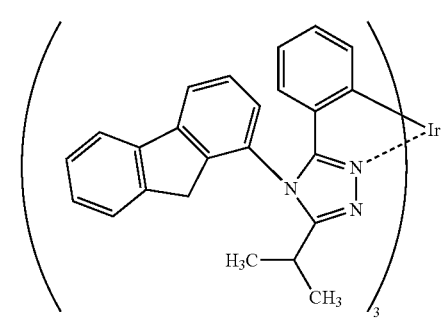

(117) 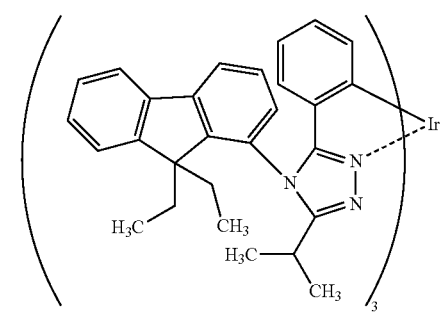

(118) 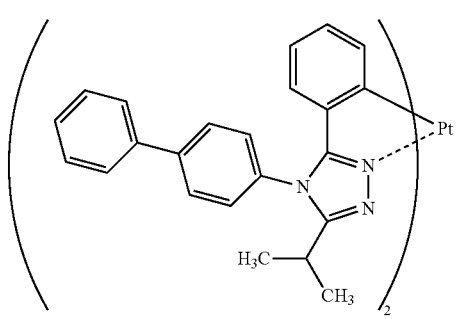

(119) 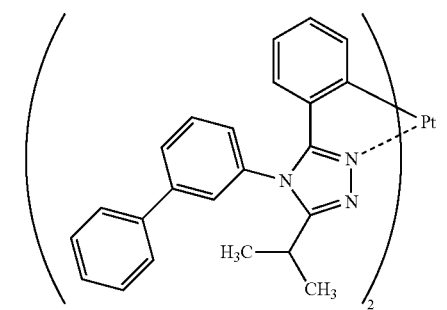

(120) 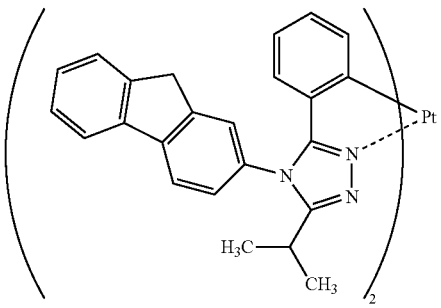

(121) 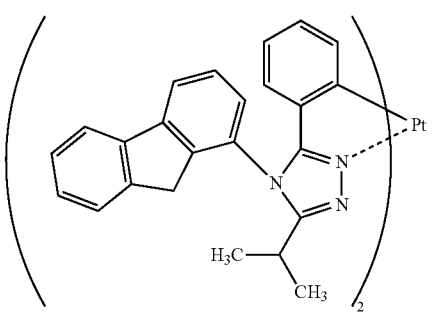

The above organometallic complexes each of which is one embodiment of the present invention are novel substances which can emit phosphorescence.

Next, an example of a method for synthesizing an organometallic complex having the structure represented by General Formula (G1) will be described.

Step 1: Method for Synthesizing 4-biphenyl-3-phenyl4H-1,2,4-triazole derivative

First, an example of a method for synthesizing a 4-biphenyl-3-phenyl4H-1,2,4-triazole derivative represented by General Formula (G0) will be described. In General Formula (G0), $R^1$ represents an alkyl group having 1 to 4 carbon atoms. In addition, Ar represents a p-biphenyl group or an m-biphenyl group which may have a substituent. In the case where Ar has a substituent, an alkyl group having 1 to 4 carbon atoms can be used as the substituent. In the case where Ar has substituents adjacent to each other, the adjacent substituents may be bonded to form a ring.

(G0) 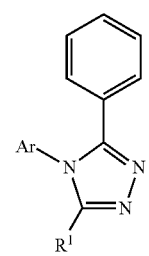

As shown in Scheme (a) below, the 4-biphenyl-3-phenyl4H-1,2,4-triazole derivative can be obtained by reacting a thioether compound including a phenyl group and a biphenyl group or an N-substituted thioamide compound including a phenyl group and a biphenyl group (A1) with an alkyl hydrazide compound (A2). In Scheme (a), $R^1$ represents an alkyl group having 1 to 4 carbon atoms, and Ar represents a p-biphenyl group or an m-biphenyl group which may have a substituent. In the case where Ar has a substituent, an alkyl group having 1 to 4 carbon atoms can be used as the substituent. In the case where Ar has substituents adjacent to each other, the adjacent substituents may be bonded to form a ring.

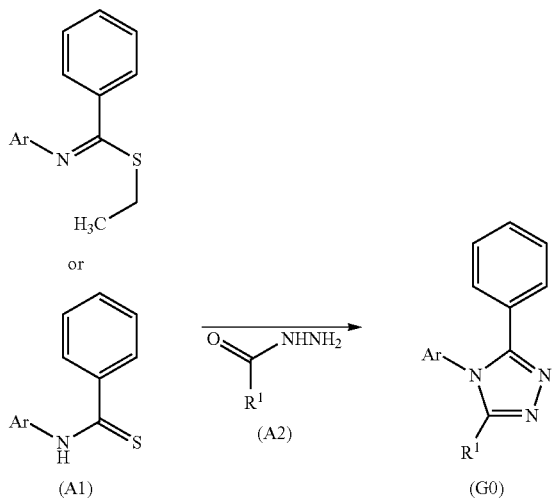

Note that the method for synthesizing the 4-biphenyl-3-phenyl4H-1,2,4-triazole derivative is not limited to Scheme (a). As another example of a synthesis method, a method in which a thioether compound including $R^1$ and a biphenyl group or an N-substituted thioamide compound including $R^1$ and a biphenyl group is reacted with a phenyl hydrazide compound. As shown in Scheme (a'), there is also a method in which a dihydrazide compound (A1') is reacted with a primary amine compound (A2'). In Scheme (a'), $R^1$ represents an alkyl group having 1 to 4 carbon atoms. In addition, Ar represents a p-biphenyl group or an m-biphenyl group which may have a substituent. In the case where Ar has a substituent, an alkyl group having 1 to 4 carbon atoms can be used as the substituent. In the case where Ar has substituents adjacent to each other, these adjacent substituents may be bonded to form a ring.

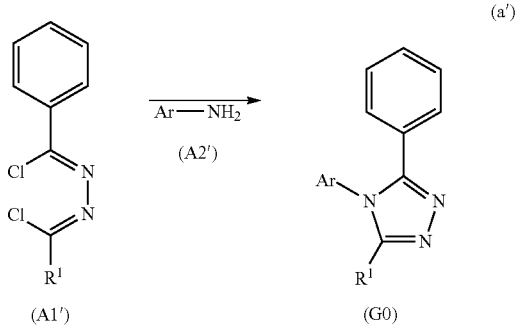

As described above, the 4-biphenyl-3-phenyl4H-1,2,4-triazole derivative can be synthesized by a very simple synthesis scheme.

Step 2: Method for Synthesizing Orthometalated Complex Having 4-biphenyl-3-phenyl4H-1,2,4-triazole Derivative as Ligand The organometallic complex having the structure represented by General Formula (G1) can be obtained in the following manner as shown in Scheme (b) below, the 4-biphenyl-3-phenyl4H-1,2,4-triazole derivative obtained in Step 1 and a metal compound of a Group 9 element or a Group 10 element, which contains halogen (e.g., rhodium chloride hydrate, palladium chloride, iridium chloride hydrate, ammonium hexachloroiridate, or potassium tetrachloroplatinate), or an organometallic complex compound of a Group 9 element or a Group 10 element (e.g., an acetylacetonate complex or a diethylsulfide complex) are mixed and then heated. This heating step may be performed after the 4-biphenyl-3-phenyl4H-1,2,4-triazole derivative, which can be obtained in Step 1, and a metal compound of a Group 9 element or a Group 10 element, which contains halogen, or an organometallic complex compound of a Group 9 element or a Group 10 element are dissolved in an alcohol-based solvent (e.g., glycerol, ethylene glycol, 2-metoxyethanol, or 2-ethoxyethanol). In Scheme (b), M represents a Group 9 element or a Group 10 element. When M is a Group 9 element, n is 3, and when M is a Group 10 element, n is 2.

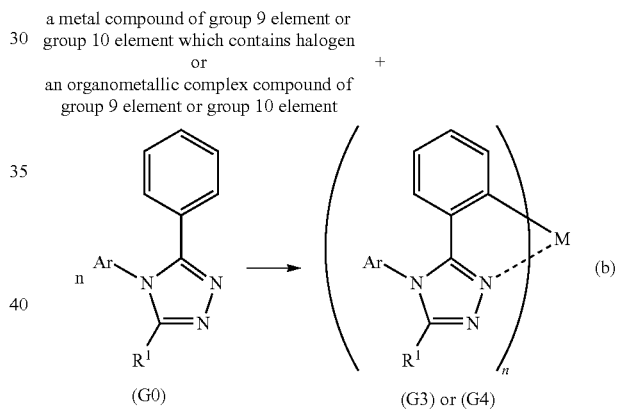

Note that the above compound (A1), (A2), (A1'), or (A2') is commercially available or can be synthesized easily.

Embodiment 2

An embodiment of a light-emitting element which is one embodiment of the present invention and includes any of the organometallic complexes described in Embodiment 1 will be described with reference to FIG. 1A.

The light-emitting element includes a pair of electrodes (a first electrode 102 and a second electrode 104) and an EL layer 103 interposed between the pair of electrodes. The light-emitting element described in this embodiment is provided over a substrate 101.

A substrate 101 is used as a support of the light-emitting element. As the substrate 101, a glass substrate, a plastic substrate, or the like can be used. As the substrate 101, a substrate having flexibility (flexible substrate) or a substrate having a curved surface can also be used. A substrate other than the above substrates can also be used as the substrate 101 as long as it functions as a support of the light-emitting element.

One of the first electrode 102 and the second electrode 104 serves as an anode and the other serves as a cathode. In this embodiment, the first electrode 102 is used as the anode and the second electrode 104 is used as the cathode; however, the present invention is not limited to this structure.

It is preferable to use a metal, an alloy, or a conductive compound, a mixture thereof, or the like having a high work function (specifically, 4.0 eV or higher) as a material for the anode. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like are given. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like are given.

It is preferable to use a metal, an alloy, or a conductive compound, a mixture thereof, or the like having a low work function (specifically, 3.8 eV or lower) as a material for the cathode. Specifically, an element belonging to Group 1 or 2 of the periodic table, such as lithium (Li), cesium (Cs), magnesium (Mg), calcium (Ca), or strontium (Sr), can be given. An alloy containing the above element (e.g., MgAg or AlLi) can also be used. Moreover, a rare earth metal such as europium (Eu) or ytterbium (Yb), or an alloy containing a rare earth metal can also be used.

In the case where an electron-injection layer in contact with the second electrode 104 is provided as part of the EL layer 103, the second electrode 104 can be formed using a variety of conductive materials such as Al, Ag or ITO, regardless of their work functions. Films of these conductive materials can be formed by a sputtering method, an inkjet method, a spin coating method, or the like.

Although the EL layer 103 can be formed to have a single-layer structure, it is normally formed to have a stacked-layer structure. There is no particular limitation on the stacked-layer structure of the EL layer 103. The EL layer 103 may be formed by combining, as appropriate, a layer containing a substance having a high electron-transport property (electron-transport layer) or a layer containing a substance having a high hole-transport property (hole-transport layer), a layer containing a substance having a high electron-injection property (electron-injection layer), a layer containing a substance having a high hole-injection property (hole-injection layer), a layer containing a bipolar substance (substance having high electron- and hole-transport properties), a layer containing a light-emitting material (light-emitting layer), and the like. For example, the EL layer 103 can be formed by combining, as appropriate, a hole-injection layer, a hole-transport layer, a light-emitting layer, an electron-transport layer, an electron-injection layer, and the like. FIG. 1A illustrates as the EL layer 103 formed over the first electrode 102, a structure in which a hole-injection layer 111, a hole-transport layer 112, a light-emitting layer 113, and an electron-transport layer 114 are sequentially stacked.

A light-emitting element emits light when current flows due to a potential difference generated between the first electrode 102 and the second electrode 104, and holes and electrons are recombined in the light-emitting layer 113 containing a substance having a high light-emitting property. In other words, a light-emitting region is formed in the light-emitting layer 113.

The emitted light is extracted out through one or both of the first electrode 102 and the second electrode 104. Thus, one or both of the first electrode 102 and the second electrode 104 are light-transmissive electrodes. In the case where only the first electrode 102 is a light-transmitting electrode, light is extracted from the substrate side through the first electrode 102. Meanwhile, in the case where only the second electrode 104 is a light-transmitting electrode, light is extracted from the side opposite to the substrate side through the second electrode 104. Moreover, in the case where the first electrode 102 and the second electrode 104 are both light-transmitting electrodes, light is extracted from both of the substrate side and the side opposite to the substrate side through the first electrode 102 and the second electrode 104.

The organometallic complex represented by General Formula (G1) can be used, for example, for the light-emitting layer 113. In this case, the light-emitting layer 113 may be formed using a thin film containing the organometallic complex represented by General Formula (G1), or may be formed using a thin film in which a host material is doped with the organometallic complex represented by General Formula (G1). When the light-emitting layer 113 is formed using the thin film in which a host material is doped with the organometallic complex, an alkyl group for $R^1$ in General Formula (G1) is preferably a branched alkyl group. The branched alkyl group suppresses the entry of carriers into the organometallic complex due to steric hindrance, and thus has an effect of decreasing the carrier trapping property of the organometallic complex and reducing the driving voltage of the element as a result. Thus, it is more preferable to use an isopropyl group, an isobutyl group, a tert-butyl group, or a neopentyl group as the alkyl group for $R^1$.

In order to suppress energy transfer from an exciton which is generated in the light-emitting layer 113, the hole-transport layer 112 or the electron-transport layer 114 which is in contact with the light-emitting layer 113, particularly a carrier- (electron- or hole-) transport layer in contact with a side closer to a light-emitting region in the light-emitting layer 113, is preferably formed using a substance having a larger energy gap than a light-emitting material contained in the light-emitting layer or an emission center substance contained in the light-emitting layer.

The hole-injection layer 111 contains a substance having a high hole-injection property, and has a function of helping injection of holes from the first electrode 102 to the hole-transport layer 112. By providing the hole-injection layer 111, a difference in ionization potential between the first electrode 102 and the hole-transport layer 112 is relieved, so that holes are easily injected. The hole-injection layer 111 is preferably formed using a substance having smaller ionization potential than a substance contained in the hole-transport layer 112 and having larger ionization potential than a substance contained in the first electrode 102, or a substance in which an energy band is bent when the substance being provided as a thin film with a thickness of 1 to 2 nm between the hole-transport layer 112 and the first electrode 102. In other words, a material for the hole-injection layer 111 is preferably selected so that the ionization potential of the hole-injection layer 111 is relatively smaller than that of the hole-transport layer 112. Specific examples of substances having a high hole-injection property include phthalocyanine (abbreviation: $H_2Pc$), a phthalocyanine-based compound such as copper phthalocyanine (abbreviation: CuPc), a high molecular compound such as poly(ethylenedioxythiophene)/poly(styrenesulfonate) aqueous solution (PEDOT/PSS), and the like.

The hole-transport layer 112 is a layer that contains a substance having a high hole-transport property. In this specification, a substance having a high hole-transport property refers to a substance in which the hole mobility is higher than the electron mobility, preferably a substance in which the value of the ratio of the hole mobility to the electron mobility (=hole mobility/electron mobility) is more than 100. A substance having a hole mobility of $1 \times 10^{-6}$ cm$^2$/Vs or higher is preferably used as a substance having a high hole-transport property. As specific examples of substances having a high hole-transport property, the following are given: 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), 1,3,5-tris[N,N-di(m-tolyl)amino]benzene (abbreviation: m-MTDAB), 4,4',4''-tris(N-carbazolyl)triphenylamine (abbreviation: TCTA), phthalocyanine (abbreviation: H$_2$Pc), copper phthalocyanine (abbreviation: CuPc), vanadyl phthalocyanine (abbreviation: VOPc), and the like. Note that the hole-transport layer 112 may have a single-layer structure or a stacked-layer structure.

The electron-transport layer 114 is a layer that contains a substance having a high electron-transport property. In this specification, a substance having a high hole-transport property refers to a substance in which the electron mobility is higher than the hole mobility, preferably a substance in which the value of the ratio of the electron mobility to the hole mobility (=electron mobility/hole mobility) is more than 100. A substance having an electron mobility of $1 \times 10^{-6}$ cm$^2$/Vs or higher is preferably used as a substance having a high electron-transport property. Specific examples of the substances having a high electron-transport property include a metal complex having a quinoline skeleton, a metal complex having a benzoquinoline skeleton, a metal complex having an oxazole-based ligand, and a metal complex having a thiazole-based ligand. As specific examples of metal complexes having a quinoline skeleton, the following are given: tris(8-quinolinolato)aluminum (abbreviation: Alq), tris(4-methyl-8-quinolinolato)aluminum (abbreviation: Almq$_3$), and bis(2-methyl-8-quinolinolato)(4-phenylphenolato)aluminum (abbreviation: BAlq). As a specific example of a metal complex having a benzoquinoline skeleton, bis(10-hydroxybenzo[h]quinolinato)beryllium (abbreviation: BeBq$_2$) is given. As a specific example of a metal complex having an oxazole-based ligand, bis[2-(2-hydroxyphenyl)benzoxazolato]zinc (abbreviation: Zn(BOX)$_2$) is given. As a specific example of a metal complex having a thiazole-based ligand, bis[2-(2-hydroxyphenypbenzothiazolato]zinc (abbreviation: Zn(BTZ)$_2$) is given. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ 01), bathophenanthroline (abbreviation: BPhen), bathocuproine (BCP), or the like can be used. The substances specifically listed above are mainly substances having an electron mobility of $1 \times 10^{-6}$ cm$^2$/Vs or higher. Note that any substance other than the above substances may be used for the electron-transport layer 114 as long as the electron-transport property is higher than the hole-transport property. Further, the electron-transport layer 114 may have a single-layer structure or a stacked-layer structure.

Further, a layer for controlling transport of electron carriers may be provided between the light-emitting layer 113 and the electron-transport layer 114. Note that the layer for controlling transport of electron carriers is a layer obtained by adding a small amount of substance having a high electron-trapping property to the above-described material having a high electron-transport property. By providing the layer for controlling transport of electron carriers, transfer of electron carriers can be suppressed and carrier balance can be adjusted. Such a structure is very effective in preventing a problem (such as reduction in element lifetime) caused when electrons pass through the light-emitting layer.

Further, an electron-injection layer may be provided in contact with the second electrode 104 between the electron-transport layer 114 and the second electrode 104. As the electron-injection layer, a layer which contains a substance having an electron-transport property and an alkali metal, an alkaline earth metal, or a compound thereof such as lithium fluoride (LiF), cesium fluoride (CsF), or calcium fluoride (CaF$_2$) may be used. By providing the electron-injection layer, electrons can be injected efficiently from the second electrode 104.

Any of a variety of methods such as a vacuum evaporation method, an inkjet method, and a spin coating method can be employed for forming the EL layer 103, regardless of whether the method is a dry process or a wet process. In the case where the EL layer 103 has a stacked-layer structure, deposition methods of the layers may be different or the same.

The first electrode 102 and the second electrode 104 may be formed by a wet process using a sol-gel method, or a wet process using a paste of a metal material. Further, the first electrode 102 and the second electrode 104 may be formed by a dry process such as a sputtering method or a vacuum evaporation method.

Embodiment 3

In this embodiment, an embodiment of a light-emitting element in which any of the organometallic complexes described in Embodiment 1 is used and a plurality of light-emitting units are stacked (this light-emitting element is hereinafter referred to as "tandem light-emitting element") will be described as one embodiment of the present invention with reference to FIG. 1B. The tandem light-emitting element is a light-emitting element including a plurality of light-emitting units between a first electrode and a second electrode. The light-emitting units can be similar to the EL layer 103 described in Embodiment 2. In other words, the light-emitting element described in Embodiment 2 has a single light-emitting unit, and the light-emitting element described in Embodiment 3 has a plurality of light-emitting units.

Figure 1B:
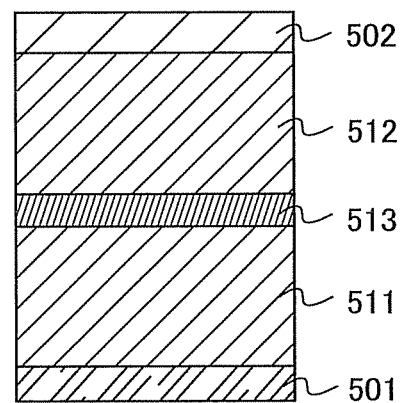

In FIG. 1B, a first light-emitting unit 511 and a second light-emitting unit 512 are stacked between a first electrode 501 and a second electrode 502. Electrodes similar to those described in Embodiment 2 can be used as the first electrode 501 and the second electrode 502. Further, the first light-emitting unit 511 and the second light-emitting unit 512 may have the same structure or different structures. One of the first light-emitting unit 511 and the second light-emitting unit 512 may have a known structure as long as the other of them has a structure similar to that in Embodiment 2.

A charge generation layer 513 is provided between the first light-emitting unit 511 and the second light-emitting unit 512. The charge generation layer 513 contains a composite material of an organic compound and a metal oxide and has a function of injecting electrons to one side of the light-emitting unit and holes to the other side of the light-emitting unit, when voltage is applied between the first electrode 501 and the second electrode 502. The composite material of an organic compound and a metal oxide is excellent in a carrier-injection property and a carrier-transport property; thus, low-voltage driving and low-current driving can be achieved.

It is preferable to use an organic compound which has a hole-transport property and has a hole mobility of $10^{-6}$ cm$^2$/

Vs or higher as the organic compound. Specific examples of the organic compound include an aromatic amine compound, a carbazole compound, aromatic hydrocarbon, and a high molecular compound (e.g., an oligomer, a dendrimer, and a polymer). An oxide of a metal belonging to any of Groups 4 to 8 in the periodic table is preferable as the metal oxide; specifically, vanadium oxide, niobium oxide, tantalum oxide, chromium oxide, molybdenum oxide, tungsten oxide, manganese oxide, and rhenium oxide are preferable because of their high electron-accepting properties. In particular, molybdenum oxide is preferable because it is stable in the air, has a low hygroscopic property, and is easily handled.

The charge generation layer 513 may have a single-layer structure or a stacked-layer structure. For example, the charge generation layer 513 may have a structure in which a layer containing a composite material of an organic compound and a metal oxide and a layer containing one compound selected from electron-donating substances and a compound having a high electron-transport property are stacked; or a structure in which a transparent conductive film and a layer containing a composite material of an organic compound and a metal oxide are stacked.

In this embodiment, the light-emitting element including two light-emitting units is described; however, the present invention is not limited to this structure. In other words, a tandem light-emitting element may be a light-emitting element including three or more light-emitting units. Note that the light-emitting element including three or more light-emitting units includes a charge generation layer between the light-emitting units. For example, a light-emitting element may be manufactured which includes a first unit formed using an organometallic complex of one embodiment of the present invention and a second unit formed using a light-emitting material which emits light with a longer wavelength than the organometallic complex (e.g., red light). A light-emitting element may also be manufactured which includes a first unit formed using an organometallic complex of one embodiment of the present invention, a second unit formed using a first light-emitting material which emits light with a longer wavelength than the organometallic complex (e.g., red light), and a third unit formed using a second light-emitting material which emits light with a longer wavelength than the organometallic complex and a shorter wavelength than the first light-emitting material (e.g., green light). By using these light-emitting elements, a white light-emitting device can be obtained.

A plurality of light-emitting units which are partitioned by a charge generation layer are arranged between a pair of electrodes in the tandem light-emitting element according to this embodiment, whereby the tandem light-emitting element can emit light with high luminance while the current density is being kept low. In addition, the tandem light-emitting element can have a long lifetime.

Embodiment 4

In this embodiment, as one embodiment of the present invention, a passive matrix light-emitting device and an active matrix light-emitting device each of which is a light-emitting device manufactured using a light-emitting element including any of the organometallic complexes described in Embodiment 1 will be described.

FIGS. 2A to 2D and FIG. 3 illustrate examples of the passive-matrix light-emitting device.

In a passive-matrix (also called simple-matrix) light-emitting device, a plurality of anodes arranged in stripes (in stripe form) are provided to be perpendicular to a plurality of cathodes arranged in stripes. At their intersections, a light-emitting layer is interposed. Thus, a pixel at an intersection of an anode which is selected (to which a voltage is applied) and a cathode which is selected emits light.

Figure 2A:
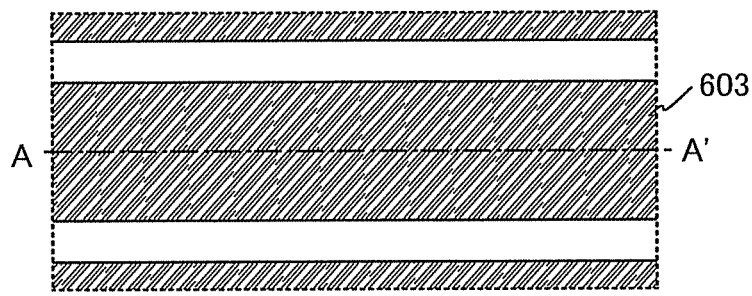
FIGS. 2A to 2D illustrate an example of a light-emitting device according to one embodiment of the present invention.
Figure 2B:
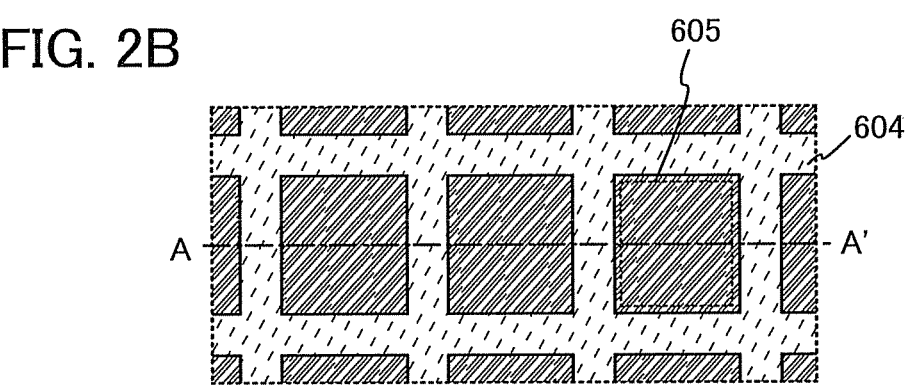
Figure 2C:
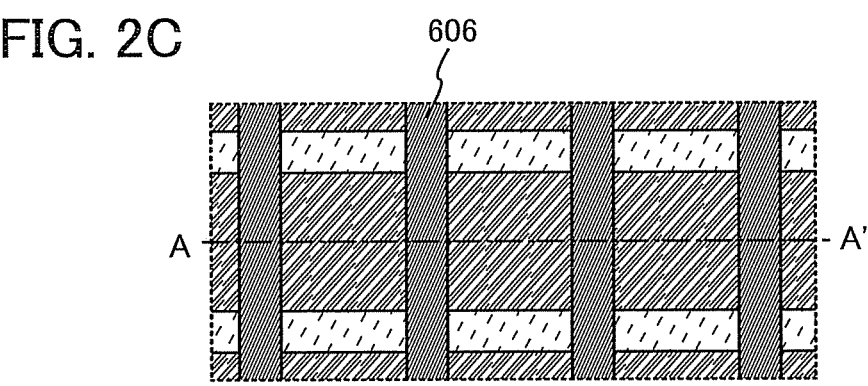
Figure 2D:
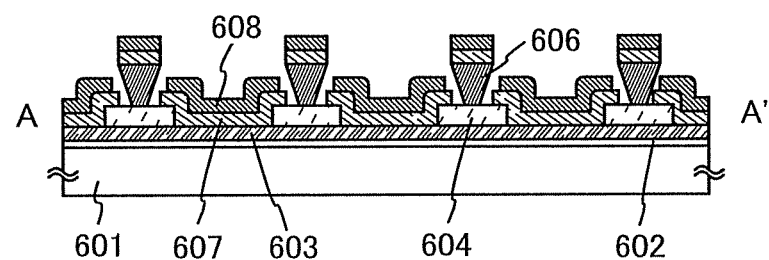

FIGS. 2A to 2C are top views of a pixel portion before sealing. FIG. 2D is a cross-sectional view along chain line A-A' in FIGS. 2A to 2C.

Over a substrate 601, an insulating layer 602 is formed as a base insulating layer. Note that the insulating layer 602 is not necessarily formed. Over the insulating layer 602, a plurality of first electrodes 603 are arranged in stripes at regular intervals (FIG. 2A). Note that each of the first electrodes 603 in this embodiment corresponds to the first electrode 501 in Embodiment 3.

In addition, a partition 604 having openings 605 corresponding to pixels is provided over the first electrodes 603. The partition 604 is formed using an insulating material. For example, polyimide, acrylic, polyamide, polyimide amide, a resist, a photosensitive or non-photosensitive organic material such as benzocyclobutene, or an SOG film such as a $SiO_x$ film containing an alkyl group can be used as the insulating material. Note that the openings 605 corresponding to pixels serve as light-emitting regions (FIG. 2B).

Over the partition 604 having openings, a plurality of partitions 606 are provided to intersect with the first electrodes 603 (FIG. 2C). The plurality of partitions 606 are formed in parallel to each other, and are inversely tapered.

Over the partition 604 and each of the first electrodes 603, an EL layer 607 and a second electrode 608 are sequentially stacked (FIG. 2D). Note that the EL layer 607 in this embodiment corresponds to the EL layer 103 in Embodiment 3, and the second electrode 608 in this embodiment corresponds to the second electrode 502 in Embodiment 3. The total height of the partition 604 and the partition 606 is set to be greater than the total thickness of the EL layer 607 and the second electrode 608; thus, as illustrated in FIG. 2D, the EL layer 607 and the second electrode 608 are each divided into a plurality of regions. Note that the plurality of divided regions are electrically isolated from one another.

The second electrodes 608 are formed in stripes and extend in the direction in which they intersect with the first electrodes 603. Note that part of the EL layers 607 and part of conductive layers forming the second electrodes 608 are formed over the inversely tapered partitions 606; however, they are separated from the EL layers 607 and the second electrodes 608.

In addition, if necessary, a sealing material such as a sealing can or a glass substrate may be attached to the substrate 601 by an adhesive agent for sealing so that the light-emitting element can be disposed in the sealed space. This can prevent the deterioration of the light-emitting element. The sealed space may be filled with filler or a dry inert gas. Further, a desiccant or the like is preferably put between the substrate and the sealing material to prevent the deterioration of the light-emitting element due to moisture or the like. The desiccant removes a minute amount of moisture, thereby achieving sufficient desiccation. As the desiccant, oxide of an alkaline earth metal such as calcium oxide or barium oxide, zeolite, or silicagel can be used. Oxide of an alkaline earth metal adsorbs moisture by chemical adsorption, and zeolite and silicagel adsorb moisture by physical adsorption.

Figure 3:
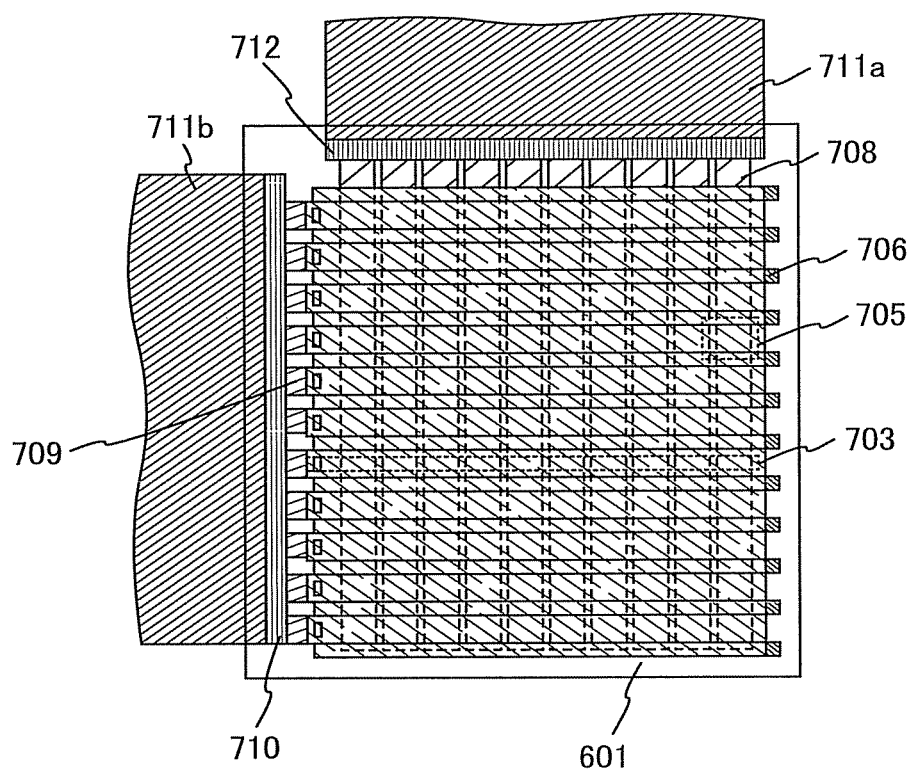
FIG. 3 illustrates an example of a light-emitting device according to one embodiment of the present invention.

FIG. 3 is a top view of the passive-matrix light-emitting device illustrated in FIGS. 2A to 2D that is provided with a flexible printed circuit (FPC) or the like.

As illustrated in FIG. 3, in a pixel portion forming an image display, scan lines and data lines interest at right angles.

The second electrode 608, the first electrode 603, and the inversely tapered partition 606 in FIGS. 2A to 2D respectively correspond to a scan line 703, a data line 708, and a partition 706 in FIG. 3. The EL layers 607 illustrated in FIG. 2D are interposed between the data lines 708 and the scanning lines 703, and an intersection indicated by a region 705 corresponds to one pixel.

The scan lines 703 are electrically connected at their ends to connection wirings 709, and the connection wirings 709 are connected to an FPC 711b via an input terminal 710. In addition, the data line 708 is connected to an FPC 711a via an input terminal 712.

An optical film such as a polarizing plate, a circularly polarizing plate (including an elliptically polarizing plate), a retardation plate (a quarter-wave plate or a half-wave plate), or a color filter may be provided as needed. Further, an anti-reflection film may be provided in addition to the polarizing plate or the circularly polarizing plate. By providing the anti-reflection film, anti-glare treatment by which reflected light can be scattered by roughness of a surface so as to reduce reflection can be performed.

Although FIG. 3 illustrates the example in which a driver circuit is not provided over the substrate, an IC chip including a driver circuit may be mounted on the substrate.

In the case where the IC chip is mounted, a data line side IC and a scan line side IC, in each of which the driver circuit for transmitting a signal to a pixel portion is formed, are mounted on the periphery of (outside) the pixel portion. As a method for mounting an IC chip, a COG method, TCP, a wire bonding method, or the like can be employed. The TCP is a TAB tape mounted with the IC, and the TAB tape is connected to a wiring over an element formation substrate to mount the IC. The data line side IC and the scan line side IC may be formed using a silicon substrate, a silicon on insulator (SOI) substrate, a glass substrate, a quartz substrate, or a plastic substrate.

Figure 4A:
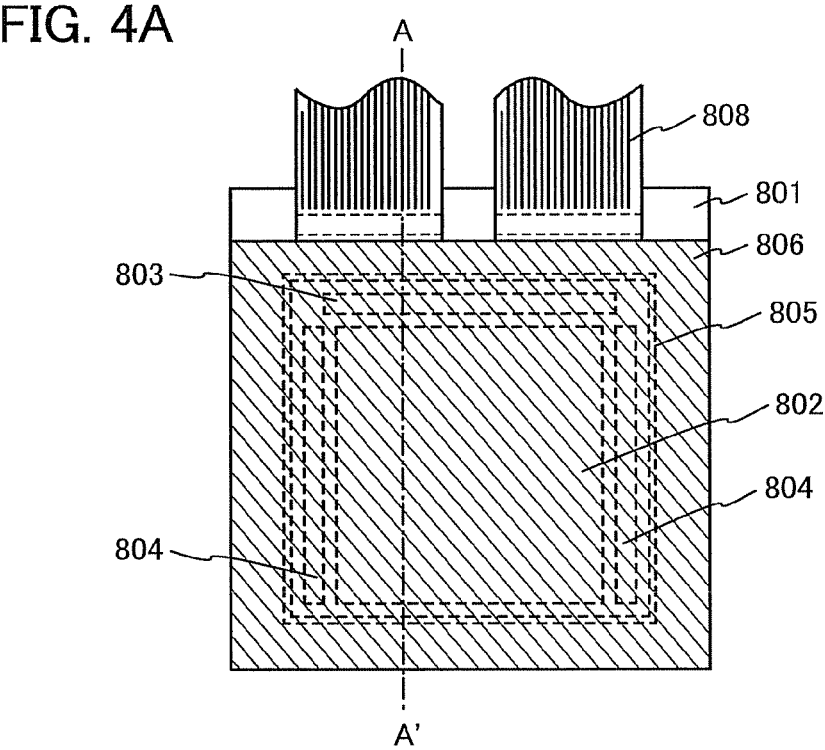
FIGS. 4A and 4B illustrate an example of a light-emitting device according to one embodiment of the present invention.
Figure 4B:
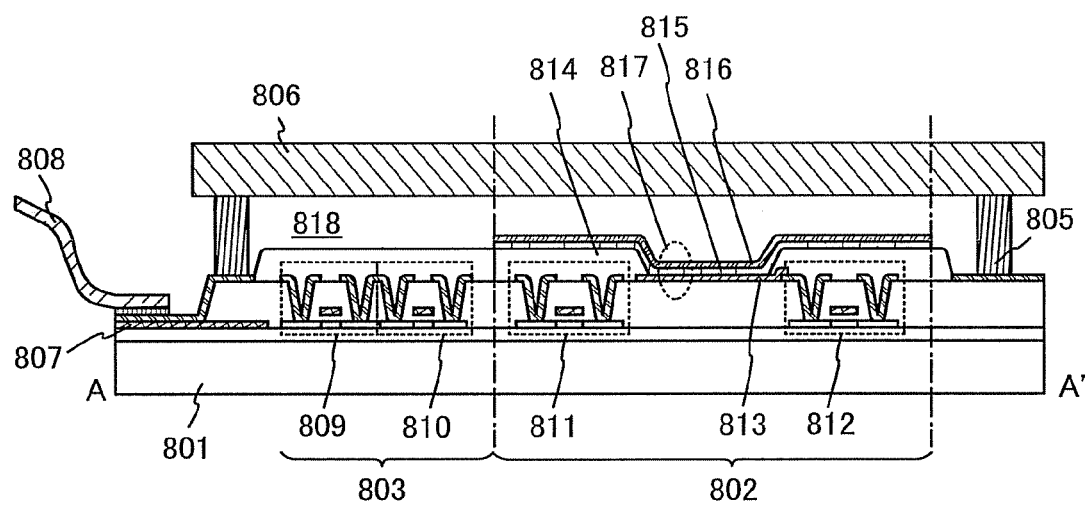

Next, an example of the active-matrix light-emitting device will be described with reference to FIGS. 4A and 4B. FIG. 4A is a top view illustrating a light-emitting device and FIG. 4B is a cross-sectional view along dashed line A-A' in FIG. 4A. The active-matrix light-emitting device of this embodiment includes a pixel portion 802 provided over an element substrate 801, a driver circuit portion (source-side driver circuit) 803, and a driver circuit portion (gate-side driver circuit) 804. The pixel portion 802, the driver circuit portion 803 and the driver circuit portion 804 are sealed between the element substrate 801 and the sealing substrate 806 by the sealing material 805.

Over the element substrate 801, a lead wiring 807 for connecting an external input terminal through which a signal (e.g., a video signal, a clock signal, a start signal, or a reset signal) or electric potential from the outside is transmitted to the driver circuit portion 803 and the driver circuit portion 804 is provided. Here, an example is described in which a FPC 808 is provided as the external input terminal. Note that although only an FPC is illustrated here, a printed wiring board (PWB) may be attached to the FPC. In this specification, the light-emitting device includes, in its category, not only a light-emitting device itself but also a light-emitting device to which an FPC or a PWB is attached.

Next, a cross-sectional structure of the active-matrix light-emitting device will be described with reference to FIG. 4B. Although the driver circuit portion 803, the driver circuit portion 804, and the pixel portion 802 are formed over the element substrate 801, the pixel portion 802 and the driver circuit portion 803 which is the source side driver circuit are illustrated in FIG. 4B.

The driver circuit portion 803 is an example where a CMOS circuit in which an n-channel TFT 809 and a p-channel TFT 810 are combined is manufactured. Note that a circuit included in the driver circuit portion can be formed using a variety of types of circuits such as a CMOS circuit, a PMOS circuit, or an NMOS circuit. In this embodiment, a driver-integrated type in which a driver circuit and the pixel portion are formed over the same substrate is described; however, the present invention is not limited to this structure, and a driver circuit can be formed over a substrate that is different from the substrate over which a pixel portion is formed.

The pixel portion 802 has a plurality of pixels, each including a switching TFT 811, a current-controlling TFT 812, and an anode 813 electrically connected to a wiring (a source electrode or a drain electrode) of the current-controlling TFT 812. An insulator 814 is formed so as to cover an end portion of the anode 813. In this embodiment, the insulator 814 is formed using a positive photosensitive acrylic resin. Note that there is no particular limitation on the structures of the TFTs such as the switching TFT 811 and the current-controlling TFT 812. For example, a staggered TFT or an inverted-staggered TFT may be employed. A top-gate TFT or a bottom-gate TFT may also be employed. There is no particular limitation also on the material of a semiconductor used for the TFTs, and silicon or an oxide semiconductor such as oxide including indium, gallium, and zinc may be used. Moreover, the crystallinity of a semiconductor used for the TFT is not particularly limited either; an amorphous semiconductor or a crystalline semiconductor may be used.

A light-emitting element 817 includes an anode 813, an EL layer 815, and a cathode 816. The structure and materials of the light-emitting element is described in Embodiment 2; therefore, the detailed description is not given here. Note that the anode 813, the EL layer 815, and the cathode 816 in FIGS. 4A and 4B respectively correspond to the first electrode 102, the EL layer 103, and the second electrode 104 in Embodiment 2. Although not illustrated, the cathode 816 is electrically connected to the FPC 808 which is an external input terminal.

The insulator 814 is provided at an end portion of the anode 813. In addition, in order that the cathode 816 which is formed over the insulator 814 at least favorably covers the insulator 814, the insulator 814 is preferably formed so as to have a curved surface with curvature at an upper end portion or a lower end portion. For example, it is preferable that the upper end portion or the lower end portion of the insulator 814 have a curved surface with a radius of curvature (0.2 μm to 3 μm). The insulator 814 can be formed using an organic compound such as a negative photosensitive resin which becomes insoluble in an etchant by light or a positive photosensitive resin which becomes soluble in an etchant by light, or an inorganic compound such as silicon oxide or silicon oxynitride can be used.

Although the cross-sectional view of FIG. 4B illustrates only one light-emitting element 817, a plurality of light-emitting elements are arranged in matrix in the pixel portion 802. For example, light-emitting elements emitting light of three kinds of colors (R, G, and B) are formed in the pixel portion 802, so that a light-emitting device capable of full-color display can be obtained. Alternatively, a light-emitting device which is capable of full-color display may be manufactured by a combination with color filters.

The light-emitting element 817 is formed in a space 818 that is surrounded by the element substrate 801, the sealing substrate 806, and the sealing material 805. The space 818 may be filled with a rare gas, a nitrogen gas, or the sealing material 805.

A material that transmits as little moisture and oxygen as possible, such as an epoxy-based resin, is preferably used as the sealing material 805. As the sealing substrate 806, a glass substrate, a quartz substrate, a plastic substrate formed of fiberglass-reinforced plastics (FRP), polyvinyl fluoride (PVF), polyester, acrylic, or the like can be used.

As described above, the active matrix light-emitting device can be obtained. In such a light-emitting device, a light-emitting element including any of the organometallic complexes with high emission efficiency described in Embodiment 1 is used; thus, the light-emitting device has low power consumption.

Embodiment 5

In this embodiment, specific examples of electronic devices and lighting devices each of which is manufactured using the light-emitting device described the above embodiment will be described with reference to FIGS. 5A to 5E and FIG. 6.

Examples of electronic devices to which the present invention can be applied include a television device (also referred to as a television or a television receiver), a monitor of a computer, cameras such as a digital camera and a digital video camera, a digital photo frame, a mobile phone, a portable game machine, a portable information terminal, an audio reproducing device, a game machine (e.g., a pachinko machine or a slot machine), a housing of a game machine, and the like. Specific examples of these electronic devices and lighting devices are illustrated in FIGS. 5A to 5E and FIG. 6.

Figure 5A:
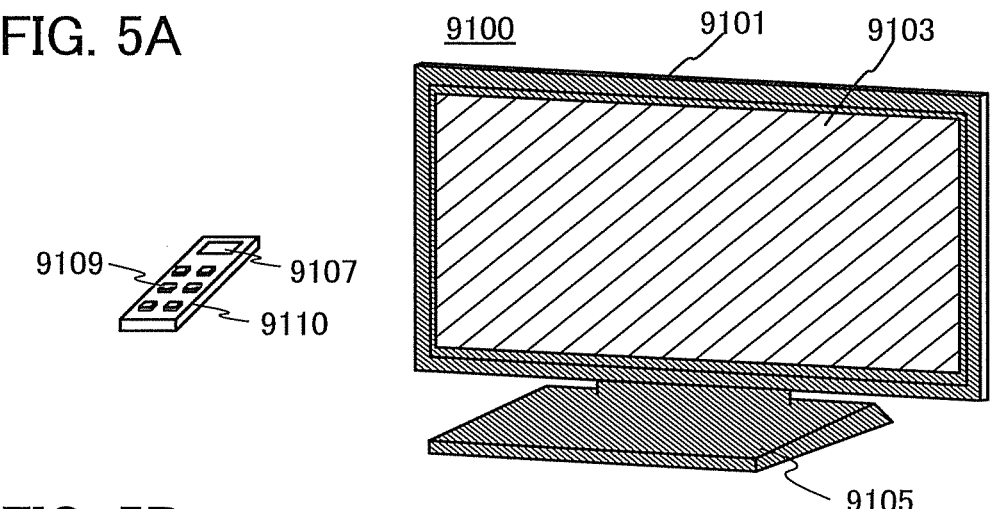
FIGS. 5A to 5E illustrate examples of electronic devices and a lighting device according to one embodiment of the present invention.

FIG. 5A illustrates a television device 9100. In the television device 9100, a display portion 9103 is incorporated in a housing 9101. A light-emitting device manufactured using one embodiment of the present invention can be used in the display portion 9103, so that an image can be displayed on the display portion 9103. Note that the housing 9101 is supported by a stand 9105 here.

The television device 9100 can be operated with an operation switch of the housing 9101 or a separate remote controller 9110. Channels and volume can be controlled with an operation key 9109 of the remote controller 9110 so that an image displayed on the display portion 9103 can be controlled. Further, the remote controller 9110 may be provided with a display portion 9107 for displaying data output from the remote controller 9110.

The television device 9100 illustrated in FIG. 5A is provided with a receiver, a modem, and the like. With the receiver, the television device 9100 can receive a general television broadcast. Further, when the television device 9100 is connected to a communication network by wired or wireless connection via the modem, one-way (from a transmitter to a receiver) or two-way (between a transmitter and a receiver or between receivers) data communication can be performed.

A light-emitting device in which a light-emitting element including any of the organometallic complexes with high emission efficiency described in Embodiment 1 is used has low power consumption; thus, when the light-emitting device is used in the display portion 9103 of the television device, the television device can have lower power consumption than conventional television devices.

Figure 5B:
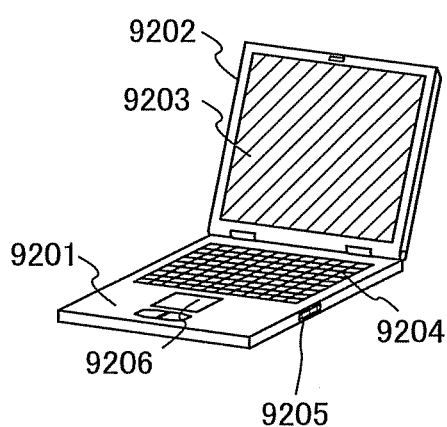

FIG. 5B illustrates a computer, which includes a main body 9201, a housing 9202, a display portion 9203, a keyboard 9204, an external connection port 9205, a pointing device 9206, and the like. The computer is manufactured using a light-emitting device manufactured using one embodiment of the present invention for the display portion 9203.

A light-emitting device in which a light-emitting element including any of the organometallic complexes with high emission efficiency described in Embodiment 1 is used has low power consumption; thus, when the light-emitting device is used in the display portion 9203 of the computer, the computer can have lower power consumption than conventional computers.

Figure 5C:
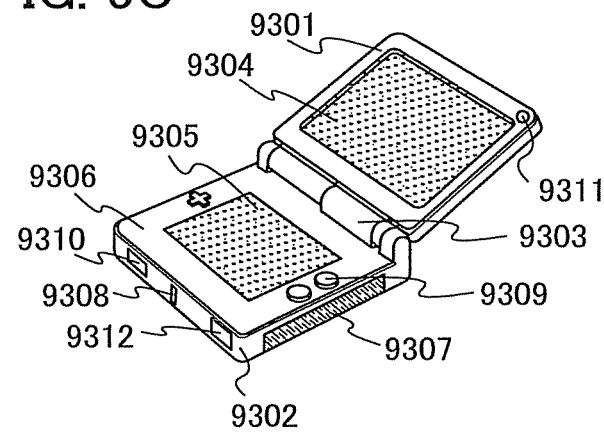

FIG. 5C illustrates a portable game machine, which includes two housings, a housing 9301 and a housing 9302 which are jointed with a connector 9303 so as to be opened and closed. A display portion 9304 is incorporated in the housing 9301, and a display portion 9305 is incorporated in the housing 9302. In addition, the portable game machine illustrated in FIG. 5C includes an input means such as operation keys 9309, a connection terminal 9310, a sensor 9311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 9312. The portable game machine may further be provided with a speaker portion 9306, a recording medium insertion portion 9307, an LED lamp 9308, and the like. Needless to say, the structure of the portable amusement machine is not limited to the above, and it is acceptable as long as the light-emitting device manufactured using any of the above embodiments is used for one or both of the display portion 9304 and the display portion 9305.

The portable game machine illustrated in FIG. 5C has a function of reading a program or data stored in a recording medium to display it on the display portion, and a function of sharing information with another portable game machine by wireless communication. Note that a function of the portable game machine illustrated in FIG. 5C is not limited to the above, and the portable game machine can have a variety of functions.

A light-emitting device in which a light-emitting element including any of the organometallic complexes with high emission efficiency described in Embodiment 1 is used has low power consumption; thus, when the light-emitting device is used in the display portions (9304 and 9305) of the portable game machine, the portable game machine can have lower power consumption than conventional portable game machines.

Figure 5D:
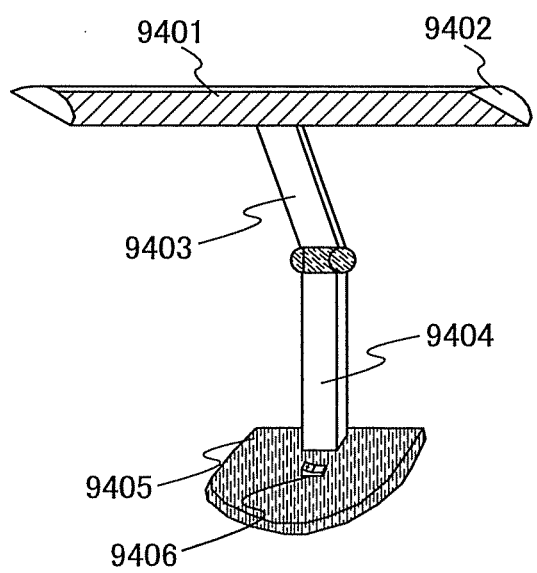
Figure 5E:
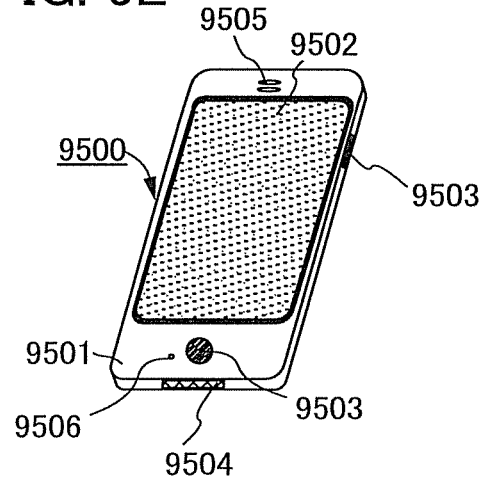

FIG. 5E illustrates an example of a mobile phone. A mobile phone 9500 is provided with a display portion 9502 incorporated in a housing 9501, operation buttons 9503, an external connection port 9504, a speaker 9505, a microphone 9506, and the like. Note that the mobile phone 9500 is manufactured using a light-emitting device manufactured using one embodiment of the present invention for the display portion 9502.

Users can input data, make a call, or texting by touching the display portion 9502 of the mobile phone 9500 illustrated in FIG. 5E with their fingers or the like.

There are mainly three screen modes for the display portion 9502. The first mode is a display mode mainly for displaying images. The second mode is an input mode mainly for inputting data such as characters. The third mode is a display-and-input mode in which two modes of the display mode and the input mode are combined.

For example, in the case of making a call or texting, a text input mode mainly for inputting characters is selected for the display portion 9502 so that characters displayed on a screen can be input. In this case, a keyboard or number buttons are preferably displayed on almost the entire screen of the display portion 9502.

By providing a detection device which includes a sensor for detecting inclination, such as a gyroscope or an acceleration sensor, inside the mobile phone 9500, the direction of the mobile phone 9500 (whether the mobile phone 9500 is placed horizontally or vertically for a landscape mode or a portrait mode) is determined so that display on the screen of the display portion 9502 can be automatically switched.

In addition, the screen mode is switched by touching the display portion 9502 or operating the operation buttons 9503 of the housing 9501. Alternatively, the screen modes can be switched depending on the kind of image displayed on the display portion 9502. For example, when a signal of an image displayed on the display portion is a signal of moving image data, the screen mode is switched to the display mode; when the signal is a signal of text data, the screen mode is switched to the input mode.

Moreover, in the input mode, when input by touching the display portion 9502 is not performed within a specified period of time while a signal detected by an optical sensor in the display portion 9502 is detected, the screen mode may be controlled so as to be switched from the input mode to the display mode.

The display portion 9502 can also function as an image sensor. For example, an image of a palm print, a fingerprint, or the like is taken by touching the display portion 9502 with the palm or the finger, whereby personal authentication can be performed. Further, by providing a backlight or a sensing light source which emits a near-infrared light in the display portion, an image of a finger vein, a palm vein, or the like can be taken.

A light-emitting device in which a light-emitting element including any of the organometallic complexes with high emission efficiency described in Embodiment 1 is used has low power consumption; thus, when the light-emitting device is used in the display portion 9502 of the mobile phone, the mobile phone can have lower power consumption than conventional mobile phones.

FIG. 5D illustrates a tabletop lighting device including a lighting portion 9401, a shade 9402, an adjustable aim 9403, a support 9404, a base 9405, and a power supply switch 9406. The tabletop lighting device is manufactured using a light-emitting device manufactured using one embodiment of the present invention for the lighting portion 9401. Note that the modes of the lighting device is not limited to tabletop lighting devices, but include ceiling-fixed lighting devices, wall-hanging lighting devices, portable lighting devices, and the like.

Figure 6:
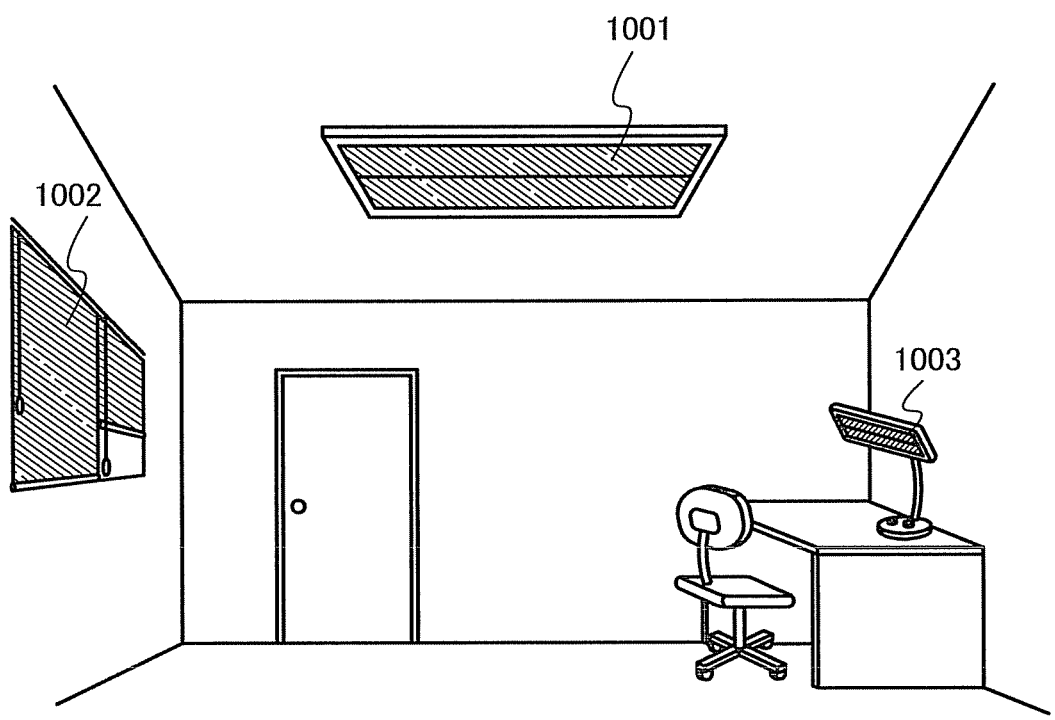
FIG. 6 illustrates examples of lighting devices according to one embodiment of the present invention.

FIG. 6 illustrates an example in which the light-emitting device manufactured using one embodiment of the present invention is used for an indoor lighting device 1001. Since the light-emitting device manufactured using one embodiment of the present invention can have a large area, the light-emitting device can be used as a lighting device having a large area. In addition, the light-emitting device described in the above embodiment can be thinned, and thus can be used as a roll-up type lighting device 1002. As illustrated in FIG. 6, a tabletop lighting device 1003 which is the same as the tabletop lighting device illustrated in FIG. 5D may be used in a room provided with the indoor lighting device 1001.

A light-emitting device in which a light-emitting element including any of the organometallic complexes with high emission efficiency described in Embodiment 1 is used has low power consumption; thus, when the light-emitting device is used as lighting device, the lighting device can have lower power consumption than conventional lighting devices.

Figure 7:
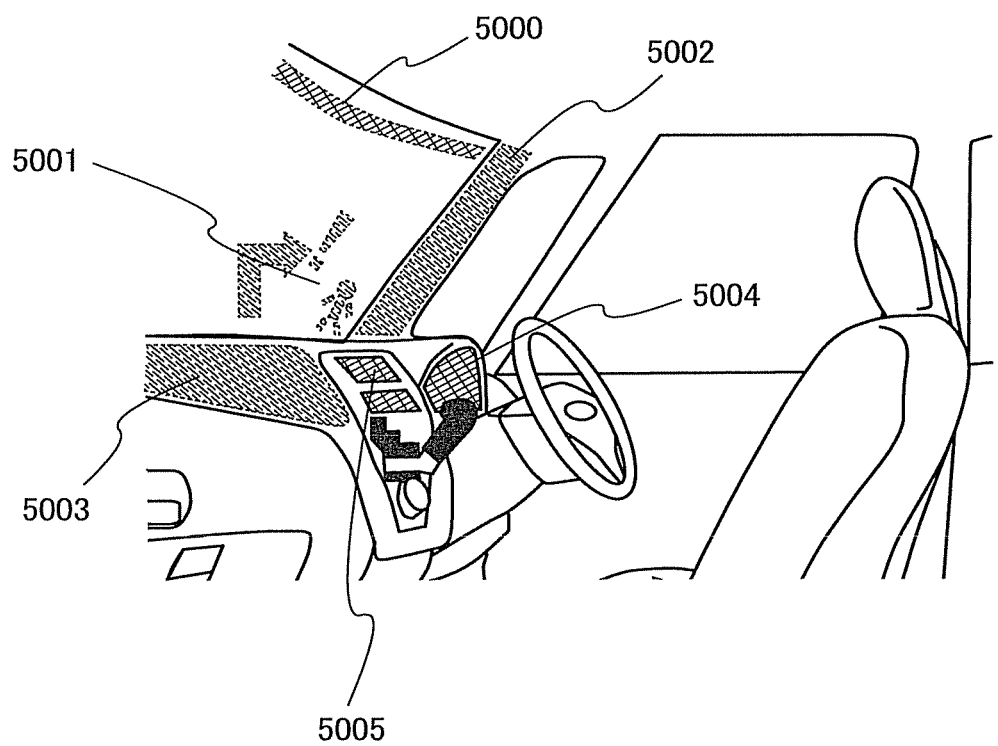
FIG. 7 illustrates examples of a vehicle-mounted display device according to one embodiment of the present invention.

The light-emitting element including any of the organometallic complexes described in Embodiment 1, which is described in Embodiment 2 or Embodiment 3, can also be used in an automobile windshield or an automobile dashboard. FIG. 7 illustrates one mode in which the light-emitting element described in Embodiment 2 or Embodiment 3 is used for an automobile windshield and an automobile dashboard. Displays 5000 to 5005 each include the light-emitting element described in Embodiment 2 or Embodiment 3.

The display 5000 and the display 5001 are display devices provided in the automobile windshield and incorporate the light-emitting element described in Embodiment 2 or Embodiment 3. The light-emitting element described in Embodiment 2 or Embodiment 3 can be formed into a so-called see-through display device, through which the opposite side can be seen, by including a first electrode and a second electrode formed with electrodes having a light-transmitting property. Such a see-through display device can be provided even in the windshield on the car, without hindering the vision. Further, for example, in the case where a transistor for driving the light-emitting element is provided, a transistor having a light-transmitting property, such as an organic transistor using an organic semiconductor material or a transistor using an oxide semiconductor, is preferably used.

The display 5002 is a display device provided in a pillar portion and incorporates light-emitting element described in Embodiment 2 or Embodiment 3. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can also be shown in the displays 5000 to 5003. Note that the displays 5000 to 5005 can also be used as lighting devices.

When the light-emitting element described in Embodiment 2 or Embodiment 3 includes any of the organometallic complexes described in Embodiment 1, the light-emitting element can have high emission efficiency and low power consumption. Therefore, even when a large number of large screens are provided, such as the displays 5000 to 5005, load on a battery can be reduced, which provides comfortable use. Thus, the light-emitting device or the lighting device using the light-emitting element described in Embodiment 2 or Embodiment 3 can be suitably used as an in-vehicle light-emitting device or lighting device.

Embodiment 6

Figure 8A:
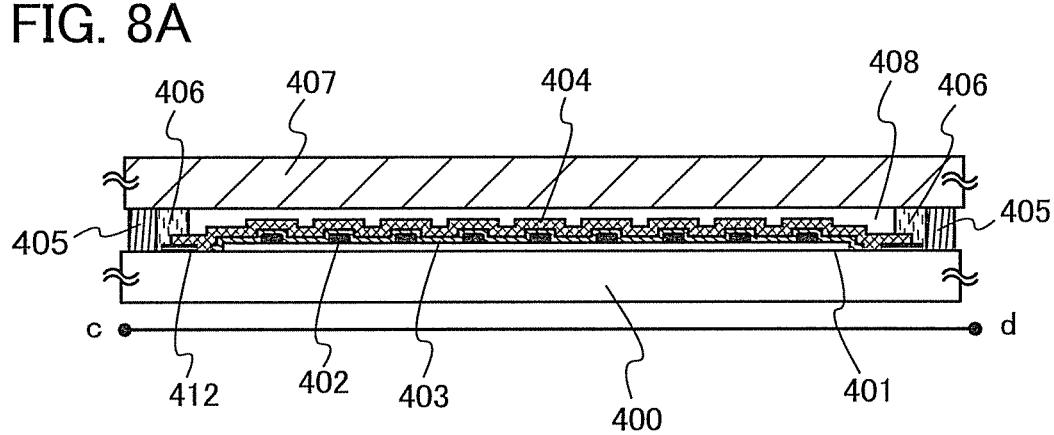
FIGS. 8A and 8B illustrate an example of a lighting device according to one embodiment of the present invention.
Figure 8B:
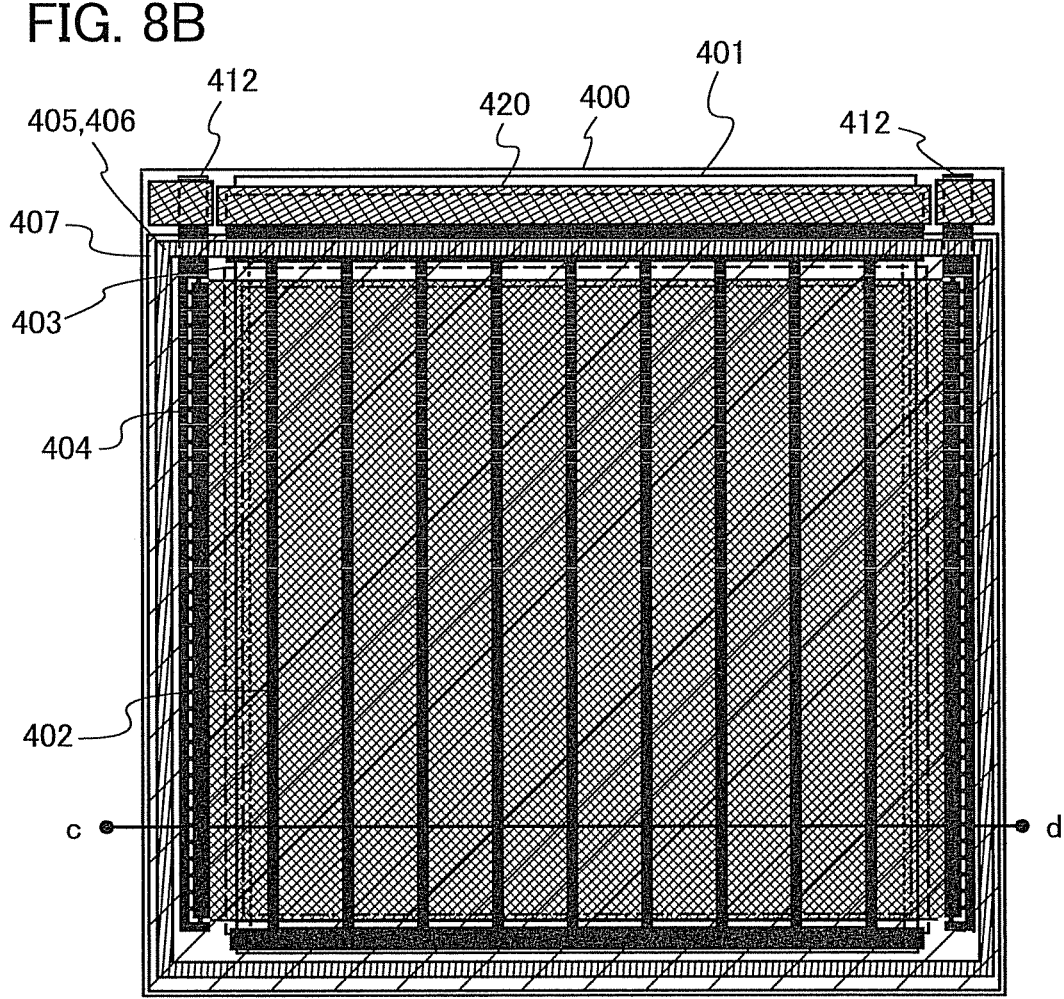

In this embodiment, an example in which a light-emitting element including any of the organometallic complexes described in Embodiment 1 is used for a lighting device will be described with reference to FIGS. 8A and 8B. FIG. 8B is a top view of the lighting device, and FIG. 8A is a cross-sectional view along line c-d in FIG. 8B.

In the lighting device in this embodiment, a first electrode 401 is formed over a substrate 400 which is a support and has a light-transmitting property. The substrate 400 and the first electrode 401 correspond to the substrate 101 and the first electrode 102 in Embodiment 2, respectively.

An auxiliary wiring 402 is provided over the first electrode 401. Since this embodiment shows an example in which light emission is extracted from the first electrode 401 side, the first electrode 401 is formed using a material having a light-transmitting property. The auxiliary wiring 402 is provided in order to compensate for low conductivity of the material having a light-transmitting property, and has a function of suppressing luminance unevenness in a light emission surface due to voltage drop caused by high resistance of the first electrode 401. The auxiliary wiring 402 is formed using a material having at least higher conductivity than the material of the first electrode 401, and is preferably formed using a material having high conductivity, such as aluminum. Note that surfaces of the auxiliary wiring 402 other than a portion thereof in contact with the first electrode 401 are preferably covered with an insulating layer. This is for suppressing light emission over the upper portion of the auxiliary wiring 402, which cannot be extracted, for reducing a reactive current, and for suppressing a reduction in power efficiency. Note that a pad 412 for applying voltage to a second electrode 404 may be formed at the same time as the formation of the auxiliary wiring 402.

An EL layer 403 is formed over the first electrode 401 and the auxiliary wiring 402. The EL layer 403 includes any of the organometallic complexes described in Embodiment 1. The EL layer 403 has a structure corresponding to the structure of the EL layer 103 in Embodiment 2 or a structure in which the light-emitting units 511 and 512 and the charge generation layer 513 in Embodiment 3 are combined. Therefore, the description in Embodiment 2 or Embodiment 3 can be referred to. Note that the EL layer 403 is preferably formed to be slightly larger than the first electrode 401 when seen from above so as to also serve as an insulating layer which prevents a short circuit between the first electrode 401 and the second electrode 404.

The second electrode 404 is formed to cover the EL layer 403. The second electrode 404 corresponds to the second electrode 104 in Embodiment 2 and has a structure similar to that of the second electrode 104. In this embodiment, it is preferable that the second electrode 404 be formed using a material having high reflectance because light emission is extracted from the first electrode 401 side. In this embodiment, the second electrode 404 is connected to the pad 412, whereby voltage is applied.

As described above, the lighting device described in this embodiment includes a light-emitting element including the first electrode 401, the EL layer 403, and the second electrode 404 (and the auxiliary electrode 402). Since the light-emitting element has high emission efficiency, the lighting device in this embodiment can be a lighting device with low power consumption. Further, the light-emitting element has high reliability; thus, the lighting device in this embodiment can be a lighting device with high reliability.

A sealing substrate 407 is fixed with sealing materials 405 and 406 so that the light-emitting element having the above structure is sealed; thus, the lighting device is completed. It is possible to use only one of the sealing material 405 and the sealing material 406. Further, the inner sealing material 406 can be mixed with a desiccant, whereby moisture is adsorbed, which results in an improvement in the reliability.

When parts of the pad 412, the first electrode 401, and the auxiliary wiring 402 are extended to the outside of the sealing materials 405 and 406, the extended parts can serve as external input terminals. An IC chip 420 mounted with a converter or the like may be provided over the external input terminals.

As described above, the lighting device described in this embodiment includes a light-emitting element including any of the organometallic complexes with high emission efficiency described in Embodiment 1, and thus can have low power consumption.

As described above, electronic devices and lighting devices can be provided using a lighting device manufactured using one embodiment of the present invention. The scope of application of the light-emitting device manufactured using one embodiment of the present invention is so wide that the light-emitting device can be applied to electronic devices in a variety of fields.

Example 1

Synthesis Example 1

In this synthesis example, an example of a synthesis of tris[4-(3-biphenyl)-5-isopropyl-3-phenyl-4H-1,2,4-triazolato]iridium (III) (abbreviation: Ir(iPrptz-3b)$_3$), an organometallic complex of one embodiment of the present invention which is represented by Structural Formula (112) in Embodiment 1, will be specifically described. Shown below is the structural formula of Ir(iPrptz-3b)$_3$.

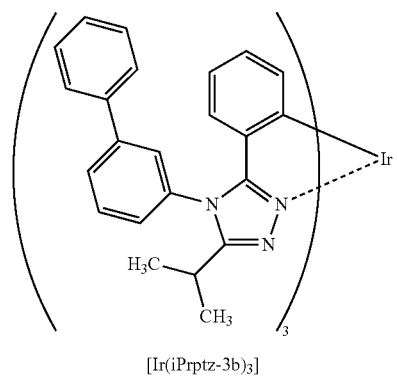

[Ir(iPrptz-3b)$_3$]

Step 1: Synthesis of N-(3-biphenyl)isobutyramide

In a 200 mL three-neck flask were put 5.0 g (30 mmol) of 3-aminobiphenyl, 4.5 g (44 mmol) of triethylamine, and 40 mL of tetrahydrofuran (THF), and the mixed solution was stirred at room temperature. Then, with a 50 mL dropping funnel, a mixed solution of 3.2 g (30 mmol) of isobutyryl chloride and 30 mL of THF was added dropwise to the mixed solution under cooling with ice, and the mixture was stirred at room temperature for 5 days. After the stirring, water was added to the resulting reaction mixture, and the mixture was subjected to extraction with chloroform. The resulting solution of the extract was washed with saturated saline, and the organic layer was dried with anhydrate magnesium sulfate. This mixture was subjected to gravity filtration, and the filtrate was concentrated to give a solid. The resulting solid was washed with a mixed solvent of chloroform and hexane and then subjected to suction filtration to give 6.9 g of a white solid of N-(3-biphenyl)isobutyramide in a yield of 98%. The synthesis scheme of Step 1 is shown in (a-1) below.

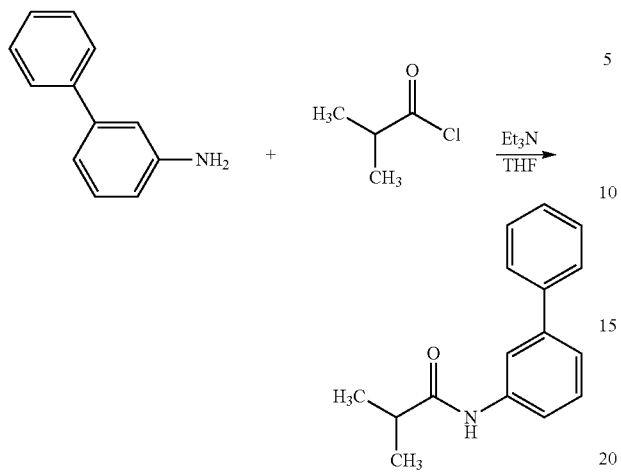

(a-1)

Step 2: Synthesis of N-(3-biphenyl)isobutyrthioamide

In a 200 mL three-neck flask were put 6.9 g (29 mmol) of N-(3-biphenyl)isobutyramide obtained in Step 1, 5.8 g (14 mmol) of 2,4-bis(4-methoxyphenyl)-1,3-dithia-2,4-diphosphetane-2,4-disulfide (Lawesson's reagent), and 70 mL of toluene, and the mixture was heated and refluxed at 120° C. for 3 hours. After that, toluene was distilled off to give a yellow oily substance. This oily substance was purified by silica gel column chromatography. Toluene was used as a developing solvent. The resulting fraction was concentrated to give 6.2 g of N-(3-biphenyl)isobutyrthioamide as a yellow oily substance in a yield of 84%. The synthesis scheme of Step 2 is shown in (a-2) below.

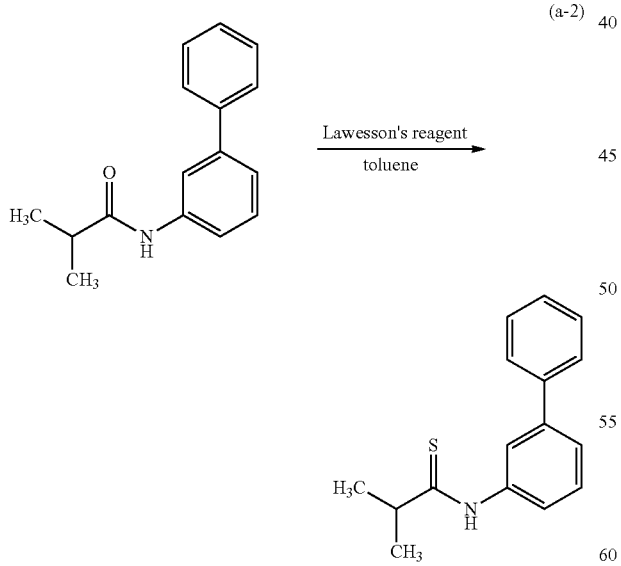

(a-2)

Step 3: Synthesis of N-[1-(ethylsulfanyl)isobutylidene]-3-biphenylamine

In a 500 mL recovery flask were put 1.7 g (24 mmol) of sodium ethoxide, 6.2 g (24 mmol) of N-(3-biphenyl)isobutyrthioamide synthesized in Step 1, and 40 mL of ethanol, and the mixture was stirred at room temperature for 12 hours. After the stirring, 2.0 mL of iodoethane was added to the mixture, and the mixture was stirred at 60° C. for 3 hours. After the stirring, ethanol was distilled off to give a brown oily substance. This oily substance was dissolved in dichloromethane, and washed with water and a saturated aqueous solution of sodium hydrogen carbonate. After the washing, anhydrous magnesium sulfate was added to the organic layer for drying. This mixture was subjected to gravity filtration, and the resulting filtrate was concentrated to give 4.3 g of N-[1-(ethylsulfanyl)isobutylidene]-3-biphenylamine as a brown oily substance in a yield of 63%. The synthesis scheme of Step 3 is shown in (a-3) below.

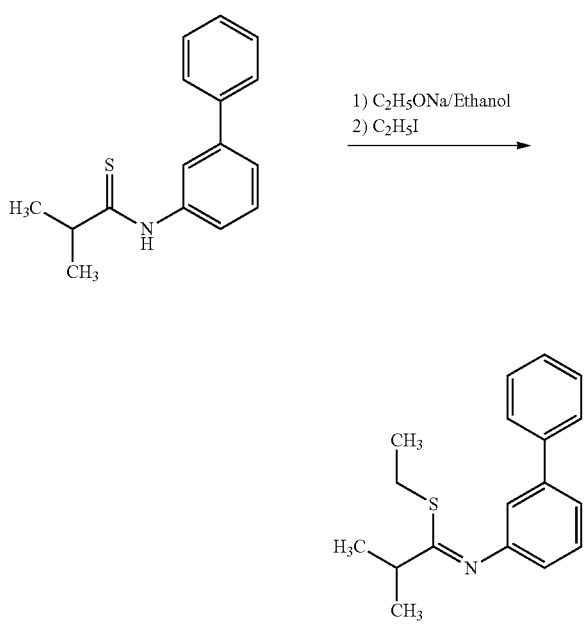

(a-3)

Step 4: Synthesis of 4-(3-biphenyl)-5-isopropyl-3-phenyl-4H-1,2,4-triazole

In a 100 mL three-neck flask were put 6.3 g (25 mmol) of N-[1-(ethylsulfanyl)isobutylidene]-3-biphenylamine, 2.9 g (21 mmol) of benzoylhydrazine, and 40 mL of 1-butanol, and the mixture was heated and refluxed at 130° C. for 10 hours. After the stirring, 1-butanol was distilled off to give a brown oily substance. The resulting oily substance was purified by silica gel column chromatography. A mixed solvent of ethyl acetate and toluene (ethyl acetate:toluene=1:3) was used as a developing solvent. The resulting fraction was concentrated to give a yellow oily substance. This oily substance was subjected to vacuum drying to precipitate a solid. A hexane suspension of this solid was irradiated with ultrasonic waves, and a white solid was collected by suction filtration, so that 3.1 g of white powder of 4-(3-biphenyl)-5-isopropyl-3-phenyl-4H-1,2,4-triazole was obtained in a yield of 53%. The synthesis scheme of Step 4 is shown in (a-4) below.

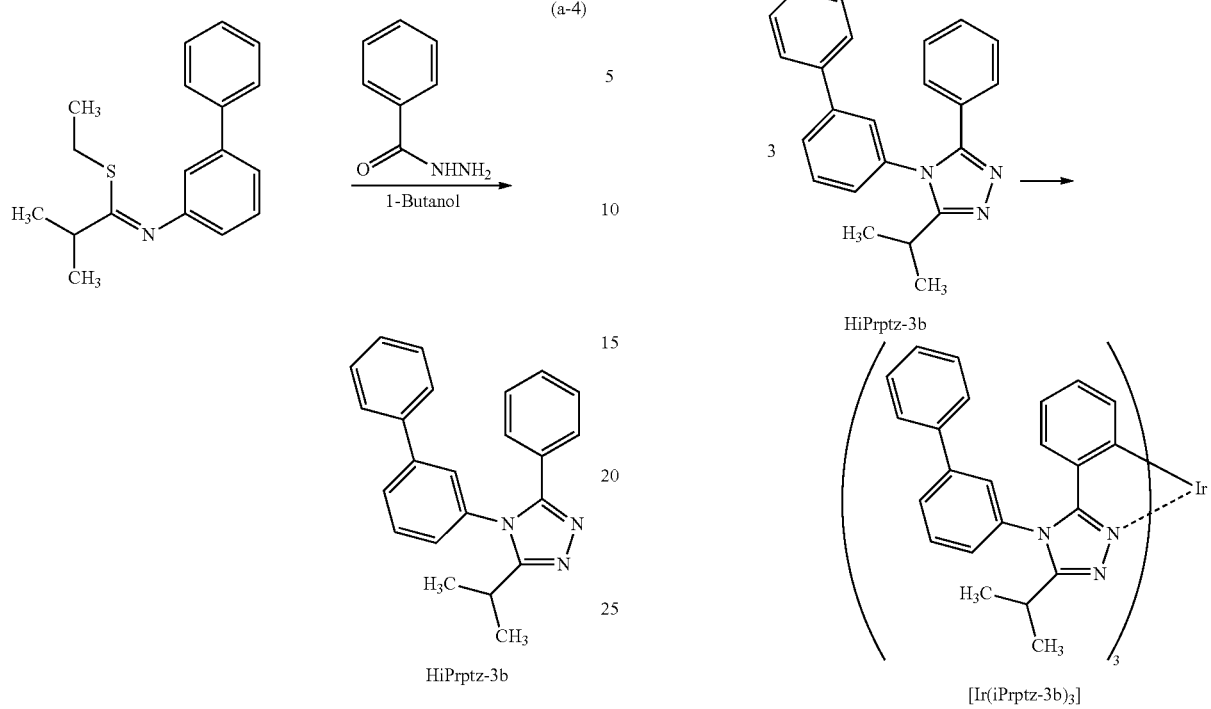

(a-4)

HiPrptz-3b

Step 5: Synthesis of tris[4-(3-biphenyl)-5-isopropyl-3-phenyl-4H-1,2,4-triazolato]iridium(III) (abbreviation: Ir(iPrptz-3b)₃)

In a reaction container provided with a three-way cock were put 2.0 g (5.9 mmol) of 4-(3-biphenyl)-5-isopropyl-3-phenyl-4H-1,2,4-triazole (abbreviation: HiPrptz-3b) obtained in Step 4 and 0.577 g (1.2 mmol) of tris(acetylacetonato)iridium(III), and the mixture was heated at 250° C. for 44 hours. The resulting reaction mixture was dissolved in dichloromethane and purified by silica gel column chromatography. A mixed solvent of dichloromethane and ethyl acetate (dichloromethane:ethyl acetate=5:1) was used as a developing solvent. The resulting fraction was concentrated to give a solid. The resulting solid was dissolved in dichloromethane, and the solution was suction-filtered through Celite (produced by Wako Pure Chemical Industries, Ltd., Catalog No. 531-16855), alumina, and Celite. The resulting filtrate was recrystallized to give a solid, and the solid was recrystallized from dichloromethane/methanol to give 0.33 g of a yellow solid in a yield of 23%. The synthesis scheme of Step 5 is shown in (a-5) below.

(a-5)

Figure 9:
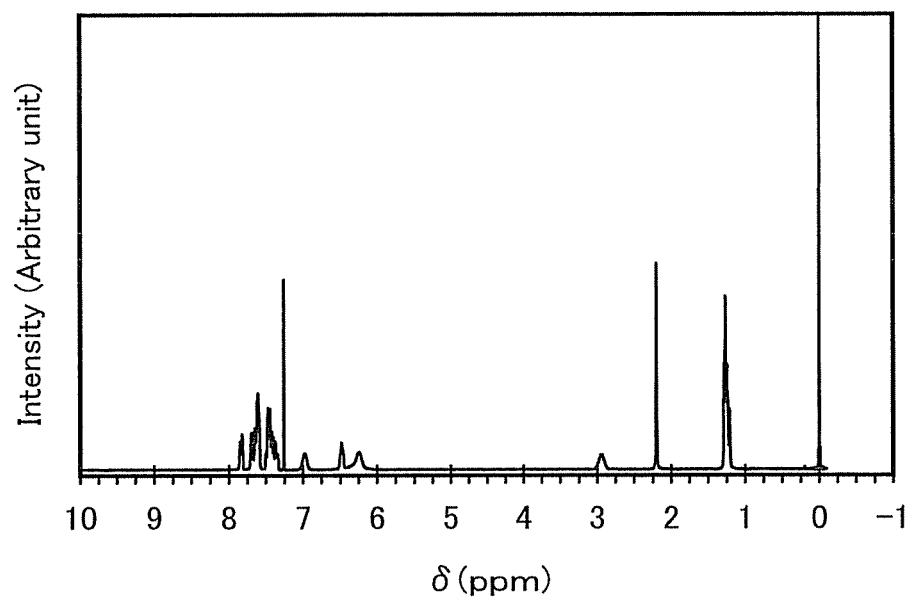
FIG. 9 is an NMR chart of Ir(iPrptz-3b)$_3$.

Analysis results by nuclear magnetic resonance spectroscopy (¹H-NMIR) of the yellow solid obtained in Step 5 are shown below. In addition, the ¹H-NMR chart is shown in FIG. 9. These results show that Ir(iPrptz-3b)₃, the organometallic complex of one embodiment of the present invention which is represented by Structural Formula (112), was obtained in Synthesis Example 1.

¹H-NMR. δ (CD₂Cl₃): 1.21-1.29 (m, 18H), 2.94 (br, 3H), 6.24 (br, 6H), 6.48 (br, 3H), 6.98 (br, 3H), 7.34-7.50 (m, 12H), 7.59-7.70 (m, 12H), 7.84 (d, 3H).

Figure 10:
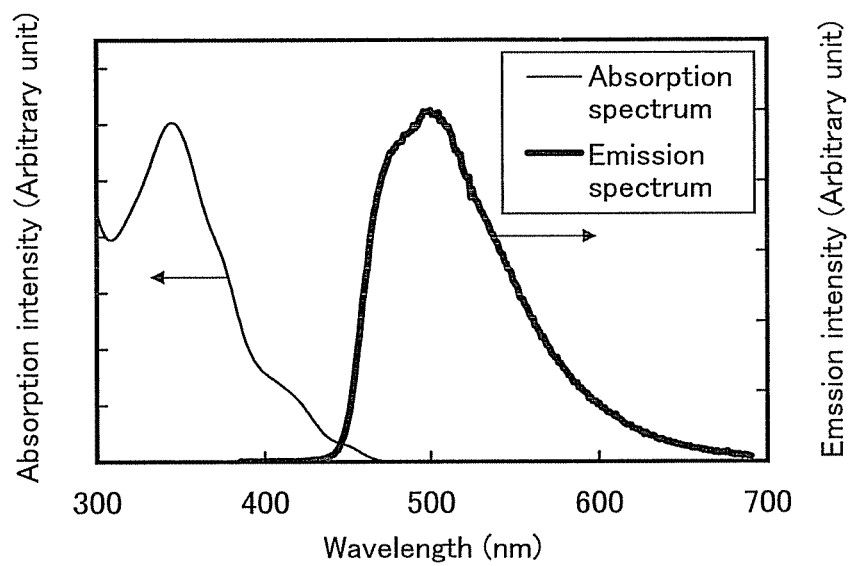
FIG. 10 shows an absorption spectrum and an emission spectrum of Ir(iPrptz-3b)$_3$.

Next, an ultraviolet-visible absorption spectrum (hereinafter, simply referred to as "absorption spectrum") and an emission spectrum of Ir(iPrptz-3b)₃ in a dichloromethane solution were measured. The absorption spectrum was measured with an ultraviolet-visible light spectrophotometer (V550 type, produced by JASCO Corporation) at room temperature in the state where the dichloromethane solution (0.112 mmol/L) was in a quartz cell. The emission spectrum was measured with a fluorescence spectrophotometer (F5920, produced by Hamamatsu Photonics K.K.) at room temperature in the state where the degassed dichloromethane solution (0.112 mmol/L) was in a quartz cell. FIG. 10 shows measurement results of the absorption spectrum and the emission spectrum. In FIG. 10, the horizontal axis represents wavelength and the vertical axis represents absorption intensity and emission intensity. In FIG. 10, two solid lines are shown: a thin line represents the absorption spectrum, and a thick line represents the emission spectrum. Note that the absorption spectrum in FIG. 10 is a result obtained in such a way that the measured absorption spectrum of only dichloromethane that was in a quartz cell was subtracted from the measured absorption spectrum of the dichloromethane solution (0.112 mmol/L) that was in a quartz cell.

As shown in FIG. 10, Ir(iPrptz-3b)₃, the organometallic complex of one embodiment of the present invention, has an emission peak at 500 nm, and blue-green emission was observed from the dichloromethane solution.

Further, quantum yield (φ) of phosphorescence of Ir(iPrptz-3b)₃ was measured. The quantum yield of phosphorescence was measured with an absolute quantum yield measurement system (C9920-02, produced by Hamamatsu Photonics K.K.) at room temperature in the state where the degassed toluene solution (0.01 mmol/L) was in a quartz cell. According to the measurement, the quantum yield of phosphorescence of Ir(iPrptz-3b)₃ was 0.82 (Φ=0.82). This result shows that Ir(iPrptz-3b)₃ is a material which emits very efficient phosphorescence.

Example 2

Synthesis Example 2

In this synthesis example, an example of a synthesis of tris[4-(4-biphenyl)-5-isopropyl-3-phenyl-4H-1,2,4-triazolato]iridium(III) (abbreviation: Ir(iPrptz-4b)₃), an organometallic complex of one embodiment of the present invention which is represented by Structural Formula (102) in Embodiment 1, will be specifically described. Shown below is the structural formula of Ir(iPrptz-4b)₃.

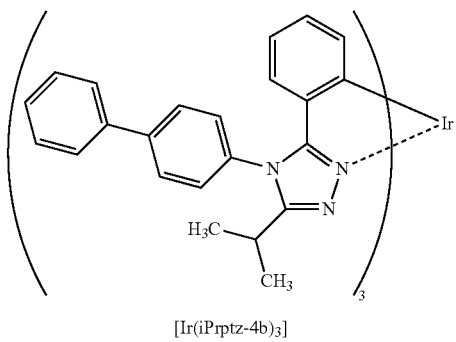

[Ir(iPrptz-4b)₃]

Step 1: Synthesis of
N-(4-bromophenyl)isobutyramide

In a 500 mL three-neck flask were put 16 g (90 mmol) of 4-bromoaniline, 11 g (108 mmol) of triethylamine, and 250 mL of tetrahydrofuran (THF), and the mixed solution was stirred. To this mixed solution, a mixed solution of 9.6 g (90 mmol) of isobutyryl chloride and 50 mL of THF was added dropwise under cooling with ice, and the mixture was stirred at room temperature for 12 hours. After the stirring, this mixture was dissolved in chloroform, and washed with water and a saturated aqueous solution of sodium hydrogen carbonate. After the washing, anhydrous magnesium sulfate was added to the organic layer for drying. The resulting mixture was subjected to gravity filtration, and the filtrate was concentrated to give a solid. This solid was washed with hexane to give 18 g of a white solid of N-(4-bromophenyl)isobutyramide in a yield of 82%. The reaction scheme of Step 1 is shown in (b-1) below.

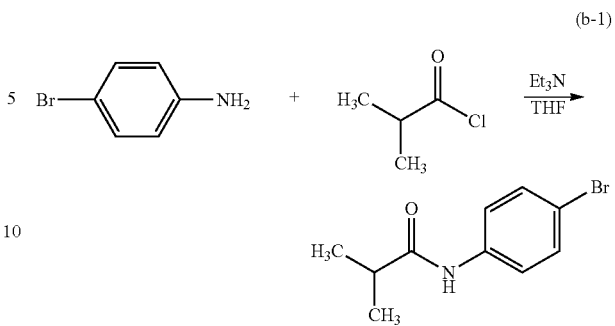

(b-1)

Step 2: Synthesis of
N-(4-bromophenyl)isobutyrthioamide

In a 500 mL three-neck flask were put 18 g (74 mmol) of N-(4-bromophenyl)isobutyramide obtained in Step 1, 15 g (37 mmol) of 2,4-bis(4-methoxyphenyl)-1,3-dithia-2,4-diphosphetane-2,4-disulfide (Lawesson's reagent), and 120 mL of toluene, and the mixture was heated and refluxed at 120° C. for 3 hours. After that, toluene was distilled off to give a yellow oily substance. This oily substance was purified by silica gel column chromatography. Toluene was used as a developing solvent. The resulting fraction was concentrated to give a yellow solid. The resulting solid was collected by suction filtration, and the collected solid was washed with a small amount of methanol to give 13 g of a white solid of N-(4-bromophenyl)isobutyrthioamide in a yield of 70%. The reaction scheme of Step 2 is shown in (b-2) below.

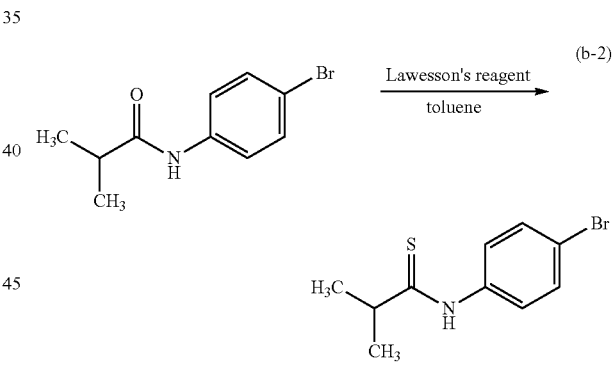

(b-2)

Step 3: Synthesis of
N-[1-(ethylsulfanyl)isobutylidene]-4-bromoaniline

In a 300 mL three-neck flask were put 3.4 g (50 mmol) of sodium ethoxide, 13 g (50 mmol) of N-(4-bromophenyl)isobutyrthioamide synthesized in Step 2, and 80 mL of ethanol, and the mixture was stirred at room temperature for 2 hours. After the stirring, 4.0 mL of iodoethane was added to this mixture, and the mixture was stirred at 60° C. for 6 hours. After the stirring, ethanol was distilled off to give a brown oily substance. This oily substance was dissolved in dichloromethane, and washed with water and a saturated aqueous solution of sodium hydrogen carbonate. After the washing, anhydrous magnesium sulfate was added to the organic layer for drying. This mixture was subjected to gravity filtration, and the resulting filtrate was concentrated to give 13 g of N-[1-(ethylsulfanyl)isobutylidene]-4-bromoaniline as a brown oily substance in a yield of 88%. The reaction scheme of Step 3 is shown in (b-3) below.

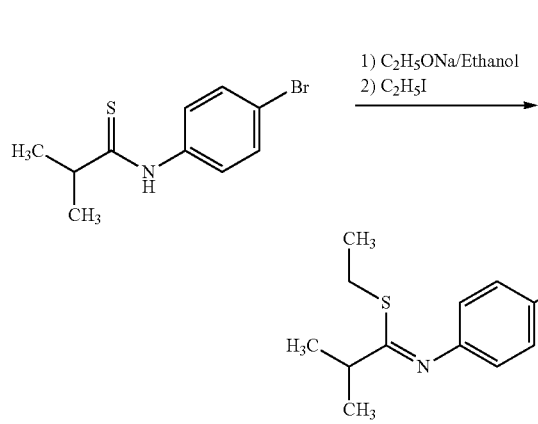

(b-3)

Step 4: Synthesis of 4-(4-bromophenyl)-5-isopropyl-3-phenyl-4H-1,2,4-triazole

In a 300 mL recovery flask were put 13 g (44 mmol) of N-[1-(ethylsulfanyl)isobutylidene]-4-bromoaniline, 3.9 g (29 mmol) of benzoylhydrazine, and 40 mL of 1-butanol, and the mixture was heated and refluxed at 130° C. for 10 hours. After that, 1-butanol was distilled off to give a solid. A methanol suspension of this solid was irradiated with ultrasonic waves, and a white solid was collected by gravity filtration, so that 2.8 g of white powder of 4-(4-bromophenyl)-5-isopropyl-3-phenyl-4H-1,2,4-triazole was obtained in a yield of 28%. The reaction scheme of Step 4 is shown in (b-4) below.

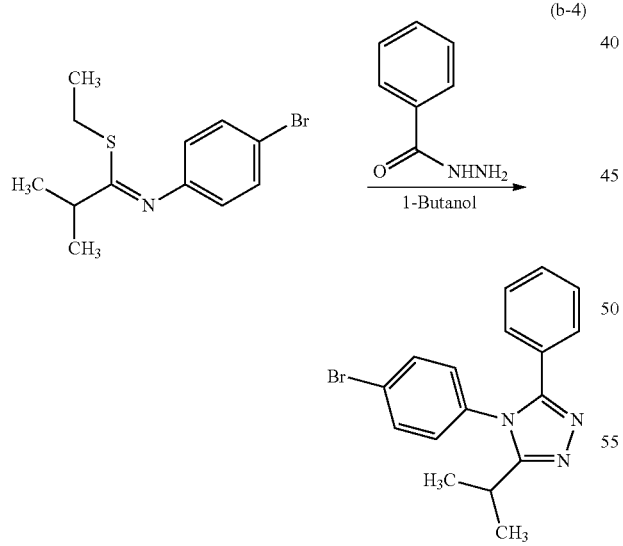

(b-4)

Step 5: Synthesis of 4-(4-biphenyl)-5-isopropyl-3-phenyl-4H-1,2,4-triazole

In a reaction container were put 2.1 g (6.1 mmol) of 4-(4-bromophenyl)-5-isopropyl-3-phenyl-4H-1,2,4-triazole synthesized in Step 4, 2.0 g (16.0 mmol) of phenylboronic acid, 0.243 g (0.8 mmol) of tri(ortho-tolyl)phosphine, 70 mL of toluene, 10 mL of ethanol, and 18 mL of 2M aqueous solution of potassium carbonate, and the atmosphere in the reaction container was replaced with nitrogen. To this mixture was added 36 mg (0.16 mmol) of palladium(II) acetate, and the mixture was heated and stirred at 80° C. for 10 hours. After the stirring, the aqueous layer and the organic layer of the resulting reaction solution was separated, and the aqueous layer was extracted with toluene. The resulting solution of the extract and the organic layer were combined and washed with a saturated aqueous solution of sodium hydrogen carbonate and then saturated saline. After the washing, anhydrate magnesium sulfate was added to the organic layer for drying, and the resulting mixture was gravity filtered to give a filtrate. The resulting filtrate was concentrated to give a crude product. The resulting crude product was purified by silica gel column chromatography. A mixed solvent of toluene and ethyl acetate (toluene:ethyl acetate=3:2) was used as a developing solvent. The resulting fraction was concentrated to give a white solid. The resulting solid was recrystallized from toluene/hexane to give 1.9 g of a white solid of 4-(4-biphenyl)-5-isopropyl-3-phenyl-4H-1,2,4-triazole in a yield of 89%. The reaction scheme of Step 5 is shown in (b-5) below.

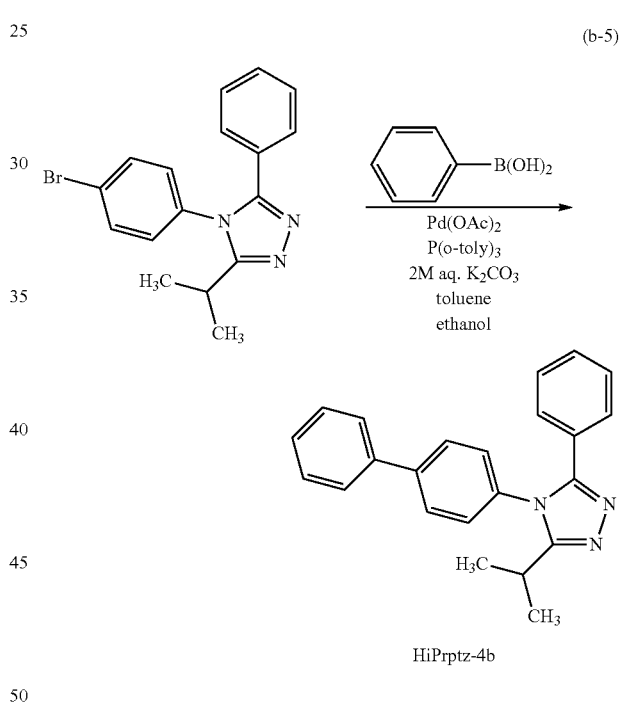

(b-5)

Step 6: Synthesis of Ir(iPrptz-4b)$_3$

In a reaction container provided with a three-way cock were put 1.8 g (5.4 mmol) of 4-(4-biphenyl)-5-isopropyl-3-phenyl-4H-1,2,4-triazole obtained in Step 5 and 0.538 g (1.1 mmol) of tris(acetylacetonato)iridium(III), and the mixture was heated at 250° C. under an argon stream for 45 hours. The resulting reaction mixture was dissolved in dichloromethane and purified by silica gel column chromatography. As a developing solvent, dichloromethane was used first, and a mixed solvent of dichloromethane and ethyl acetate (dichloromethane: ethyl acetate=10:1) was then used. The resulting fraction was concentrated to give a solid. The resulting solid was recrystallized from ethyl acetate/hexane to give 0.52 g of a yellow solid in a yield of 39%. The reaction scheme of Step 6 is shown in (b-6) below.

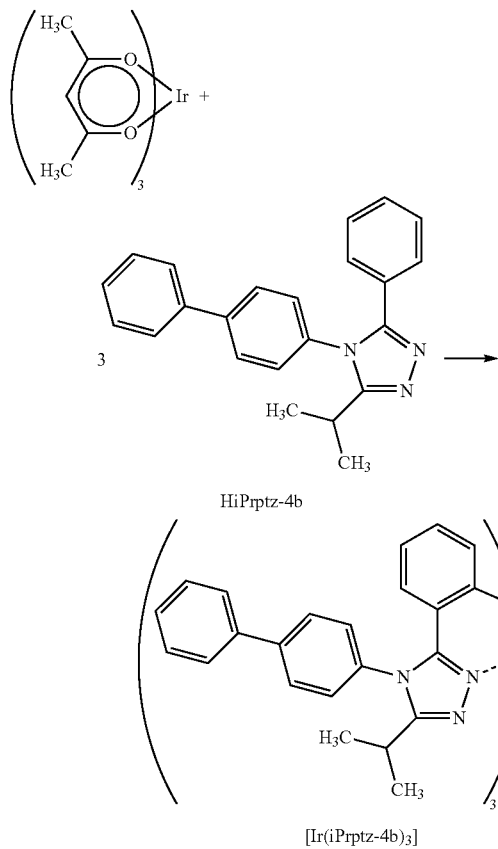

(b-6)

HiPrptz-4b

[Ir(iPrptz-4b)₃]

Figure 11:
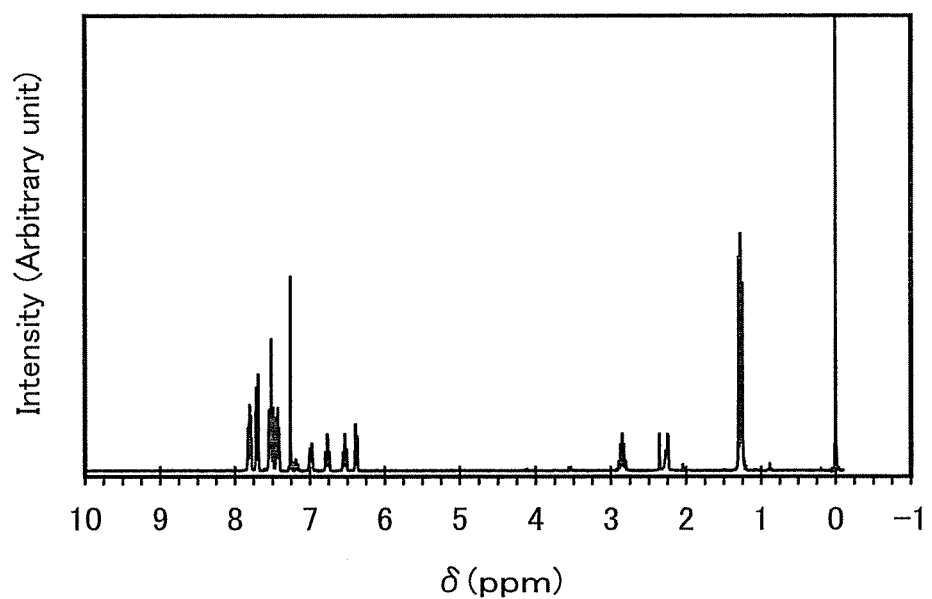
FIG. 11 is an NMR chart of Ir(iPrptz-4b)$_3$.

Analysis results by nuclear magnetic resonance spectroscopy (¹H-NMR) of the yellow solid obtained in Step 6 are shown below. In addition, the ¹H-NMR chart is shown in FIG. 11. These results show that Ir(iPrptz-4b)₃, the organometallic complex of one embodiment of the present invention which is represented by Structural Formula (102), was obtained in Synthesis Example 2.

¹H-NMR. δ CD₂Cl₂): 1.20-1.31 (m, 18H), 2.85 (sep, 3H), 6.38 (d, 3H), 6.54 (t, 3H), 6.77 (t, 3H), 6.99 (t, 3H), 7.40-7.46 (m, 6H), 7.49-7.55 (m, 9H), 7.69-7.72 (m, 6H), 7.78-7.83 (m, 6H).

Figure 12:
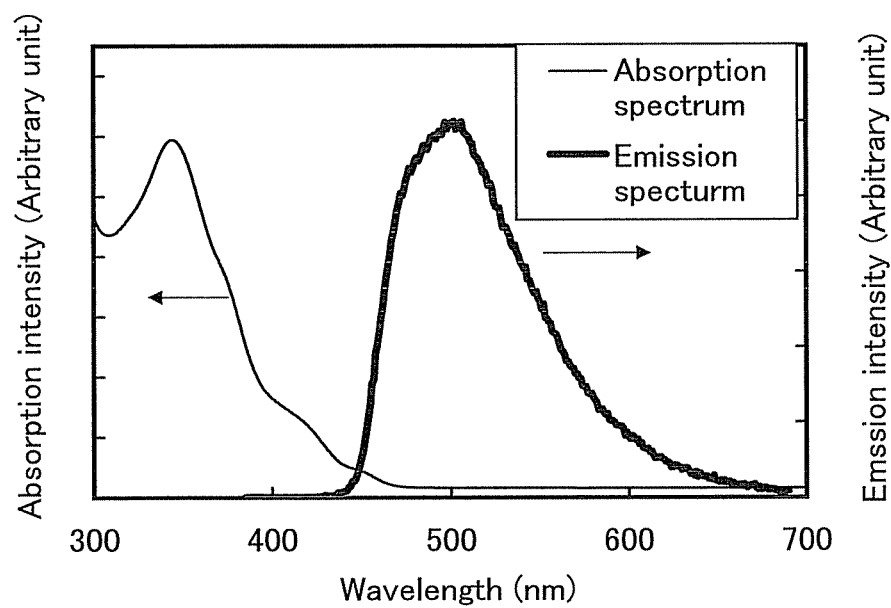
FIG. 12 shows an absorption spectrum and an emission spectrum of Ir(iPrptz-4b)$_3$.

Next, an ultraviolet-visible absorption spectrum (hereinafter, simply referred to as "absorption spectrum") and an emission spectrum of Ir(iPrptz-4b)₃ in a dichloromethane solution were measured. The absorption spectrum was measured with an ultraviolet-visible light spectrophotometer (V550 type, produced by JASCO Corporation) at room temperature in the state where the dichloromethane solution (0.103 mmol/L) was in a quartz cell. The emission spectrum was measured with a fluorescence spectrophotometer (FS920, produced by Hamamatsu Photonics K.K.) at room temperature in the state where the degassed dichloromethane solution (0.103 mmol/L) was in a quartz cell. FIG. 12 shows measurement results of the absorption spectrum and the emission spectrum. In FIG. 12, the horizontal axis represents wavelength and the vertical axis represents absorption intensity and emission intensity. In FIG. 12, two solid lines are shown: a thin line represents the absorption spectrum, and a thick line represents the emission spectrum. Note that the absorption spectrum in FIG. 12 is a result obtained in such a way that the measured absorption spectrum of only dichloromethane that was in a quartz cell was subtracted from the measured absorption spectrum of the dichloromethane solution (0.103 mmol/L) that was in a quartz cell.

As shown in FIG. 12, Ir(iPrptz-4b)₃, the organometallic complex of one embodiment of the present invention, has an emission peak at 502 nm, and blue-green emission was observed from the dichloromethane solution.

Further, quantum yield (φ) of phosphorescence of Ir(iPrptz-4b)₃ was measured. The quantum yield of phosphorescence was measured with an absolute quantum yield measurement system (C9920-02, produced by Hamamatsu Photonics K.K.) at room temperature in the state where the degassed toluene solution (0.01 mmol/L) was put in a quartz cell. According to the measurement, the quantum yield of phosphorescence of Ir(iPrptz-4b)₃ was 0.53 (Φ=0.53). This result shows that Ir(iPrptz-4b)₃ is a material which emits efficient phosphorescence.

Example 3

Synthesis Example 3

In this synthesis example, an example of a synthesis of tris [4-(9H-fluoren-2-yl)-5-isopropyl-3-phenyl-4H-1,2,4-triazolato]iridium(III) (abbreviation: Ir(iPrptz-fl)₃), an organometallic complex of one embodiment of the present invention which is represented by Structural Formula (108) in Embodiment 1, will be specifically described. Shown below is the structural formula of Ir(iPrptz-fl)₃.

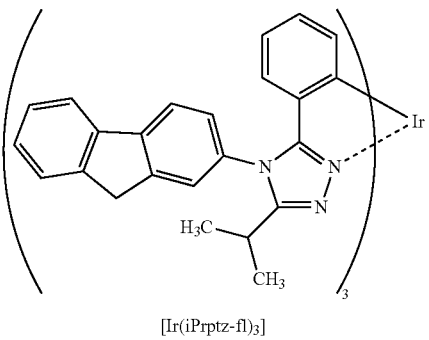

[Ir(iPrptz-fl)₃]

Step 1: Synthesis of
N-(9H-fluoren-2-yl)isobutyramide

In a 500 mL three-neck flask were put 15 g (83 mmol) of 2-aminofluorene, 10 g (100 mmol) of triethylamine, and 250 mL of tetrahydrofuran (THF), and the mixed solution was stirred. Then, to this mixed solution, a mixed solution of 8.8 g (83 mmol) of isobutyryl chloride and 50 mL of THF was added dropwise under cooling with ice, and the mixture was stirred at room temperature for 12 hours. After the stirring, 200 mL of water was added to this mixture, and the mixture was stirred for 1 hour. After the stirring, the precipitated solid was washed with water and subjected to suction filtration to give a white solid. A hexane suspension of this solid was irradiated with ultrasonic waves, and a solid was collected by suction filtration, so that 20 g of a white solid of N-(9H-fluoren-2-yl)isobutyramide was obtained in a yield of 97%. The synthesis scheme of Step 1 is shown in (c-1) below.

(c-1)

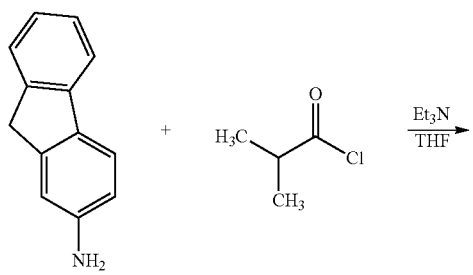

Step 2: Synthesis of
N-(9H-fluoren-2-yl)isobutyrthioamide

In a 500 mL three-neck flask were put 20 g (80 mmol) of N-(9H-fluoren-2-yl)isobutyramide, 16 g (40 mmol) of 2,4-bis(4-methoxyphenyl)-1,3-dithia-2,4-diphosphetane-2,4-disulfide (Lawesson's reagent), and 150 mL of toluene, and the mixture was heated and refluxed at 130° C. for 4 hours. After that, the precipitated solid was washed with toluene and subjected to suction filtration to give 21 g of a yellow solid of N-(9H-fluoren-2-yl)isobutyrthioamide in a yield of 100%. The synthesis scheme of Step 2 is shown in (c-2) below.

(c-2)

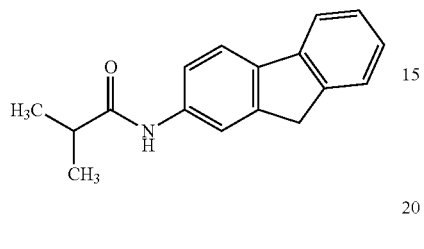

Step 3: Synthesis of 4-(9H-fluoren-2-yl)-5-isopropyl-3-phenyl-4H-1,2,4-triazole

In a 200 mL three-neck flask were put 13 g (50 mmol) of N-(9H-fluoren-2-yl)isobutyrthioamide, 8.2 g (60 mmol) of benzoylhydrazine, and 70 mL of 1-butanol, and the mixture was heated and refluxed at 130° C. for 10 hours. After that, the solid in the reaction mixture was removed by suction filtration. The resulting filtrate was concentrated to precipitate a solid. After that, 1-buthanol was distilled off to precipitate a solid. The precipitated solid was removed by suction filtration, and the filtrate was purified by silica gel column chromatography. A mixed solvent of ethyl acetate and toluene (ethyl acetate: toluene=1:1) was used as a developing solvent. The resulting fraction was concentrated to give a solid. The obtained solid was recrystallized from ethyl acetate to give 1.3 g of a white solid of 4-(9H-fluoren-2-yl)-5-isopropyl-3-phenyl-4H-1,2,4-triazole in a yield of 7%. The synthesis scheme of Step 3 is shown in (c-3) below.

(c-3)

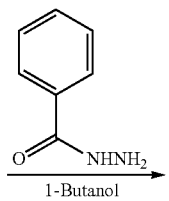

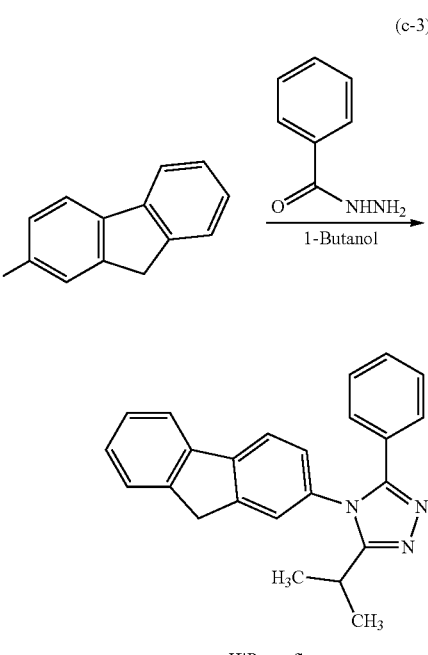

Step 4: Synthesis of Ir(iPrptz-fl)$_3$

In a reaction container provided with a three-way cock were put 2.0 g (5.9 mmol) of 4-(9H-fluoren-2-yl)-5-isopropyl-3-phenyl-4H-1,2,4-triazole and 0.587 g (1.2 mmol) of tris(acetylacetonato)iridium(III), and the mixture was heated at 250° C. under an argon stream for 36 hours. The resulting reaction mixture was dissolved in dichloromethane and purified by silica gel column chromatography. As a developing solvent, dichloromethane was used first, and a mixed solvent of dichloromethane and ethyl acetate (dichloromethane: ethyl acetate=10:1) was then used. The resulting fraction was concentrated to give a solid. The resulting solid was recrystallized from ethyl acetate/hexane to give 0.23 g of a yellow solid in a yield of 15%. The synthesis scheme of Step 4 is shown in (c-4) below.

(c-4)

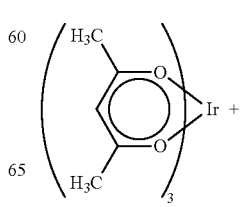

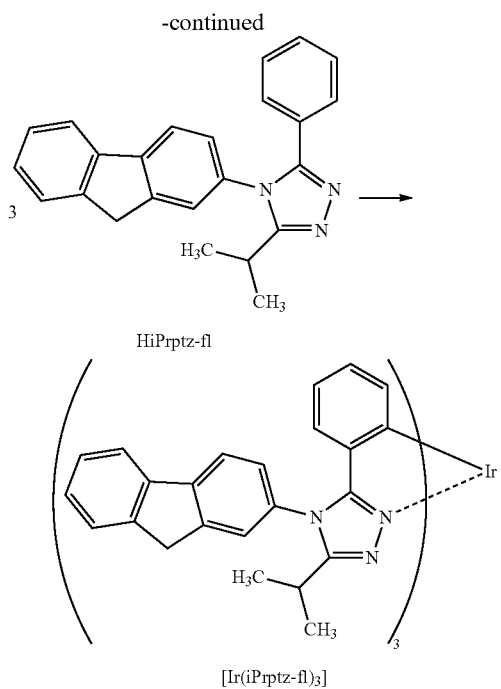

HiPrptz-fl

[Ir(iPrptz-fl)₃]

Figure 13:
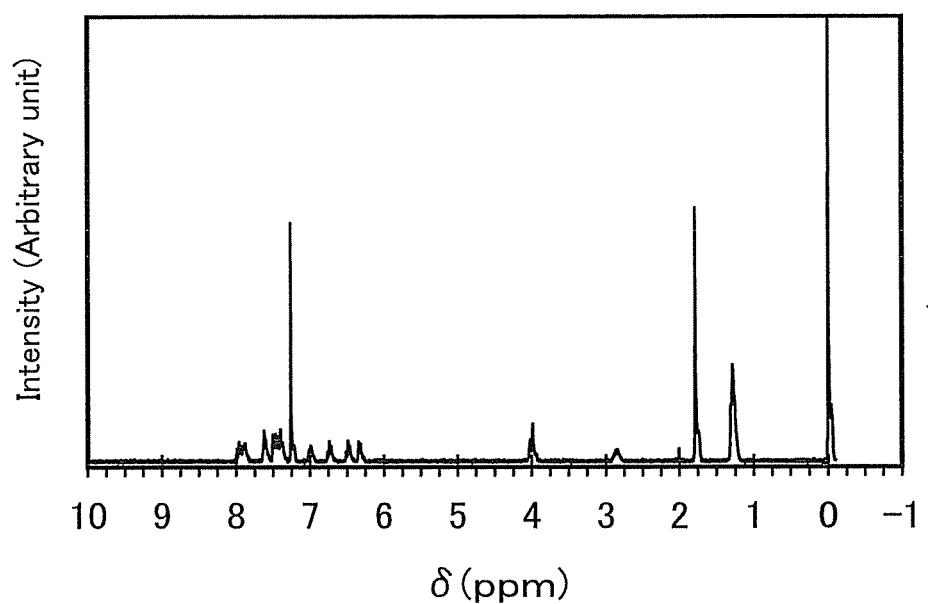
FIG. 13 is an NMR chart of Ir(iPrptz-fl)$_3$.

Analysis results by nuclear magnetic resonance spectroscopy (¹H-NMR) of the yellow solid obtained in Step 4 are shown below. In addition, the ¹NMR chart is shown in FIG. 13. These results show that Ir(iPrptz-fl)₃, the organometallic complex of one embodiment of the present invention represented by Structural Formula (108), was obtained in Synthesis Example 3.

¹H-NMR. δ (CD₂Cl₃): 1.26-1.30 (m, 18H), 2.86 (br, 3H), 4.00 (d, 6H), 6.33 (d, 3H), 6.49 (t, 3H), 6.74 (t, 3H), 6.99 (br, 3H), 7.37-7.63 (m, 15H), 7.88-7.99 (m, 6H).

Figure 14:
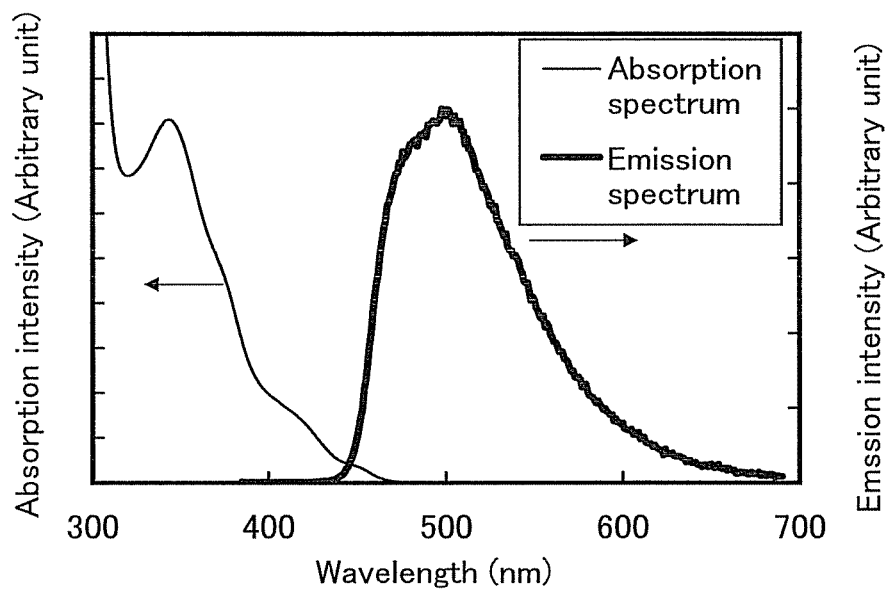
FIG. 14 shows an absorption spectrum and an emission spectrum of Ir(iPrptz-fl)$_3$.

Next, an ultraviolet-visible absorption spectrum (hereinafter, simply referred to as "absorption spectrum") and an emission spectrum of Ir(iPrptz-fl)₃ in a dichloromethane solution were measured. The absorption spectrum was measured with an ultraviolet-visible light spectrophotometer (V550 type, produced by JASCO Corporation) at room temperature in the state where the dichloromethane solution (0.133 mmol/L) was in a quartz cell. The emission spectrum was measured with a fluorescence spectrophotometer (FS920, produced by Hamamatsu Photonics K.K.) at room temperature in the state where the degassed dichloromethane solution (0.133 mmol/L) was in a quartz cell. FIG. 14 shows measurement results of the absorption spectrum and emission spectrum. In FIG. 14, the horizontal axis represents wavelength and the vertical axis represents absorption intensity and emission intensity. In FIG. 14, two solid lines are shown: a thin line represents the absorption spectrum, and a thick line represents the emission spectrum. Note that the absorption spectrum in FIG. 14 is a result obtained in such a way that the measured absorption spectrum of only dichloromethane that was in a quartz cell was subtracted from the measured absorption spectrum of the dichloromethane solution (0.133 mmol/L) that was in a quartz cell.

As shown in FIG. 14, Ir(iPrptz-fl)₃, the organometallic complex of one embodiment of the present invention, has an emission peak at 498 nm, and blue-green emission was observed from the dichloromethane solution.

Further, quantum yield (φ) of phosphorescence of Ir(iPrptz-fl)₃ was measured. The quantum yield of phosphorescence was measured with an absolute quantum yield measurement system (C9920-02, produced by Hamamatsu Photonics K.K.) at room temperature in the state where the degassed toluene solution (0.01 mmol/L) was in a quartz cell. According to the measurement, the quantum yield of phosphorescence of Ir(iPrptz-fl)₃ was 0.51 (Φ=0.51). This result shows that Ir(iPrptz-fl)₃ is a material which emits efficient phosphorescence.

Example 4

Structures, manufacturing methods, and measurement results of element characteristics of light-emitting elements each of which includes an organometallic complex of one embodiment of the present invention will be described.

Figure 15:
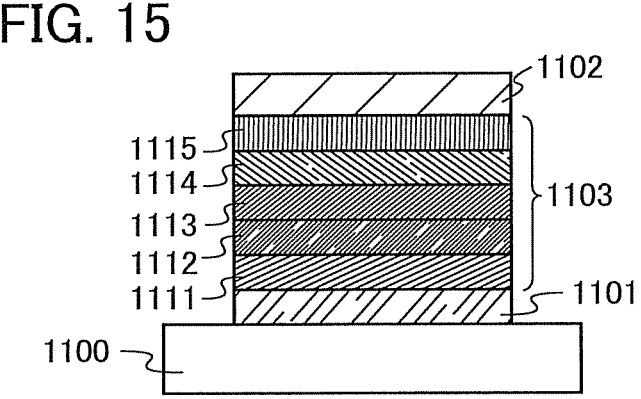
FIG. 15 is a conceptual diagram of a light-emitting element manufactured in Example 4.

FIG. 15 shows an element structure of each of a light-emitting element 1 and a light-emitting element 2 which were manufactured in this example. The light-emitting element 1 and the light-emitting element 2 each include a substrate 1100, a first electrode 1101 over the substrate 1100, an EL layer 1103 including a stack of a plurality of layers, and a second electrode 1102 over the first electrode 1101 with the EL layer 1103 interposed therebetween. In the EL layer 1103 of the light-emitting element 1 and the light-emitting element 2 of this example, a hole-injection layer 1111, a hole-transport layer 1112, a light-emitting layer 1113, an electron-transport layer 1114, and an electron-injection layer 1115 are sequentially stacked. Note that in the light-emitting layer 1113, a first light-emitting layer and a second light-emitting layer are stacked.

Table 1 shows detailed structures of the light-emitting elements manufactured. Note that the light-emitting layer 1113 was formed using an organometallic complex of one embodiment of the present invention as a light-emitting material in each of the light-emitting element 1 and the light-emitting element 2.

TABLE 1

| | First electrode | Hole-injection layer | Hole-transport layer | Light-emitting layer | | Electron-transport layer | Electron-injection layer | Second electrode |
|---|---|---|---|---|---|---|---|---|
| Light-emitting element 1 | ITSO 110 nm | CBP:MoOx (=2:1) 60 nm | mCP 20 nm | mCP: [Ir(iPrptz-3b)₃] (=1:0.08) 30 nm | mDBTBIm-II: [Ir(iPrptz-3b)₃] (=1:0.08) 10 nm | Bphen 15 nm | LiF 1 nm | Al 200 nm |
| Light-emitting element 2 | ITSO 110 nm | CBP:MoOx (=2:1) 60 nm | mCP 20 nm | mCP: [Ir(iPrptz-4b)₃] (=1:0.08) 30 nm | mDBTBIm-II: [Ir(iPrptz-4b)₃] (=1:0.08) 10 nm | Bphen 15 nm | LiF 1 nm | Al 200 nm |

Shown below are structural formulae of organic compounds used.

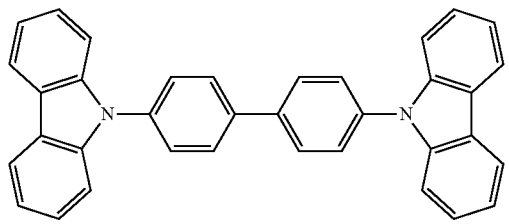

CBP

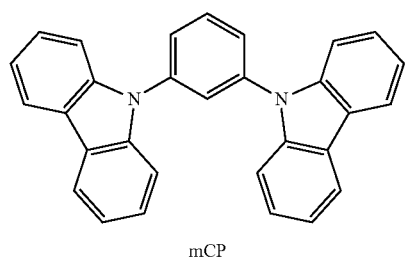

mCP

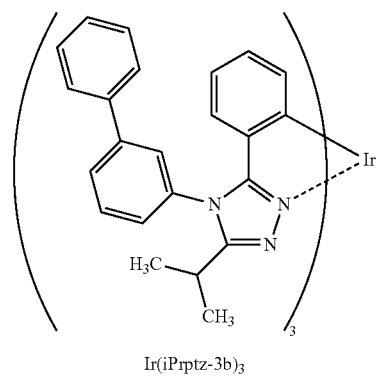

Ir(iPrptz-3b)₃

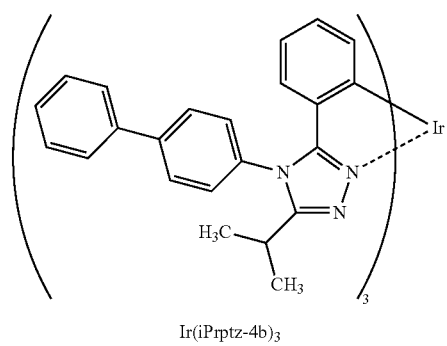

Ir(iPrptz-4b)₃

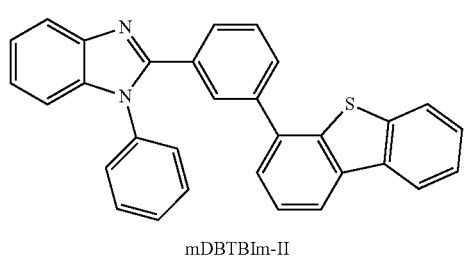

mDBTBIm-II

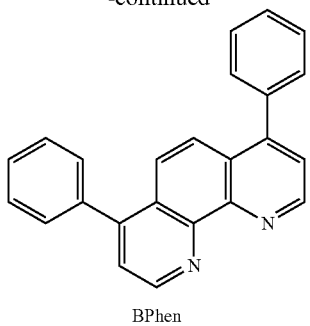

BPhen (Manufacture of Light-Emitting Element 1 and Light-Emitting Element 2)

A method for manufacturing the light-emitting element 1 and the light-emitting element 2 will be described. Note that in the light-emitting element 1, tris[4-(3-biphenyl)-5-isopropyl-3-phenyl-4H-1,2,4-triazolato]iridium(III) (abbreviation: Ir(iPrptz-3b)₃), the organometallic complex of one embodiment of the present invention which is represented by Structural Formula (112) in Embodiment 1, is included in the light-emitting layer 1113 as a light-emitting material. Note also that in the light-emitting element 2, tris [4-(4-biphenyl)-5-isopropyl-3-phenyl-4H-1,2,4-triazolato]iridium(III) (abbreviation: Ir(iPrptz-4b)₃), the organometallic complex of one embodiment of the present invention which is represented by Structural Formula (102) in Embodiment 1, is included in the light-emitting layer 1113 as a light-emitting material.

First, over the glass substrate 1100, indium tin oxide containing silicon oxide (abbreviation: ITSO) was deposited by a sputtering method, so that the first electrode 1101 which functions as an anode was formed. The thickness of the first electrode 1101 was 110 nm. The electrode area was 2 mm×2 mm.

Next, the glass substrate 1100 over which the first electrode 1101 was formed was fixed to a substrate holder provided in a vacuum evaporation apparatus such that the surface on which the first electrode 1101 was formed faced downward, and the pressure was reduced to approximately $10^{-4}$ Pa.

Next, the hole-injection layer 1111 was formed on the first electrode 1101. As the hole-injection layer 1111, a layer containing a composite material of an organic compound and an inorganic compound was formed by co-evaporation of 4,4'-di(N-carbazolyl)biphenyl (abbreviation: CBP) and molybdenum(VI) oxide. The thickness of the layer containing a composite material was 60 nm. The weight ratio of CBP to molybdenum oxide was adjusted to 2:1 (=CBP: molybdenum oxide).

Next, the hole-transport layer 1112 was formed on the hole-injection layer 1111. A 20-nm-thick film of 1,3-bis(N-carbazolyl)benzene (abbreviation: mCP) was formed as the hole-transport layer 1112 by an evaporation method using resistance heating.

Next, the light-emitting layer 1113 was formed on the hole-transport layer 1112. In the light-emitting element 1, the light-emitting layer 1113 was formed in such a manner that a 30-nm-thick film was formed by co-evaporation of mCP and Ir(iPrptz-3b)₃ and then a 10-nm-thick film was formed by co-evaporation of 2-[3-(dibenzothiophen-4-yl)phenyl]-1-phenyl-1H-benzimidazol (abbreviation: mDBTBIm-II) and Ir(iPrptz-3b)₃. The evaporation rate was adjusted so that the weight ratio of mCP to Ir(iPrptz-3b)₃ was 1:0.08 (=mCP: Ir(iPrptz-3b)₃). The evaporation rate was adjusted so that the weight ratio of mDBTBIm-II to Ir(iPrptz-3b)₃ was 1:0.08 (=mDBTBIm-II: Ir(iPrptz-3b)₃). In the light-emitting element 2, the light-emitting layer 1113 was formed in such a manner that a 30-nm-thick film was formed by co-evaporation of mCP and Ir(iPrptz-4b)₃ and then a 10-nm-thick film was formed by co-evaporation of 2-[3-(dibenzothiophen-4-yl)phenyl]-1-phenyl-1H-benzimidazol (abbreviation: mDBTBIm-II) and Ir(iPrptz-4b)₃. The evaporation rate was adjusted so that the weight ratio of mCP to Ir(iPrptz-4b)₃ was 1:0.08 (=mCP: Ir(iPrptz-4b)₃). The evaporation rate was adjusted so that the weight ratio of mDBTBIm-II to Ir(iPrptz-4b)₃ was 1:0.08 (=mDBTBIm-II: Ir(iPrptz-4b)₃).

Next, the electron-transport layer 1114 was formed on the light-emitting layer 1113. A 15-nm-thick film of bathophenanthroline (abbreviation: BPhen) was formed as the electron-transport layer 1114 by an evaporation method using resistance heating.

Next, the electron-injection layer 1115 was formed on the electron-transport layer 1114. A 1-nm-thick film of lithium fluoride (LiF) was formed as the electron-injection layer 1115 by evaporation.

Lastly, the second electrode 1102 was formed on the electron-injection layer 1115. A 200-nm-thick film of aluminum was formed as the second electrode 1102 by evaporation. Through the above steps, the light-emitting element 1 and the light-emitting element 2 were manufactured.

The thus obtained light-emitting element 1 and the light-emitting element 2 were sealed in a glove box under a nitrogen atmosphere so as not to be exposed to the air, and then operation characteristics of the light-emitting element 1 and the light-emitting element 2 were measured. Note that the measurement was carried out at room temperature (in an atmosphere kept at 25° C.).

(Evaluation Results)

Figure 16:
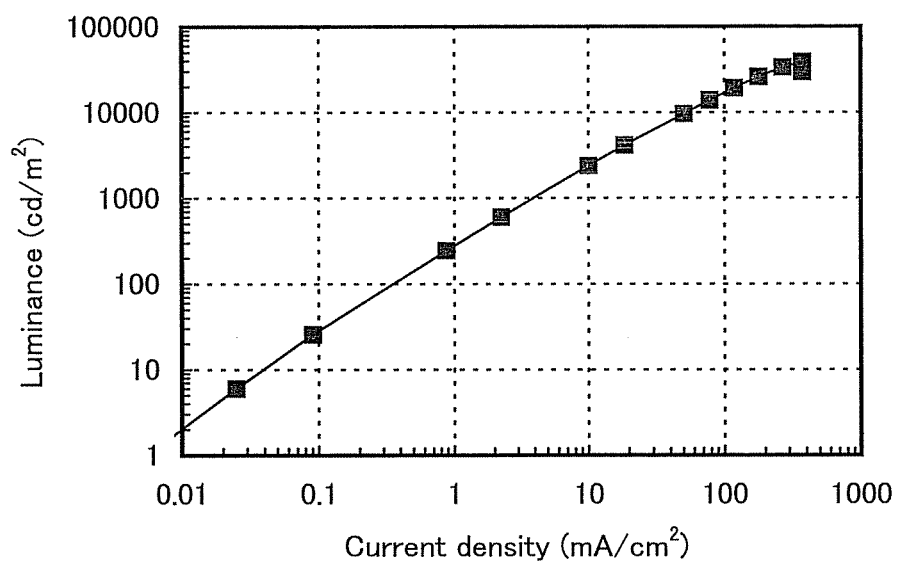
FIG. 16 shows current density-luminance characteristics of a light-emitting element 1.
Figure 17:
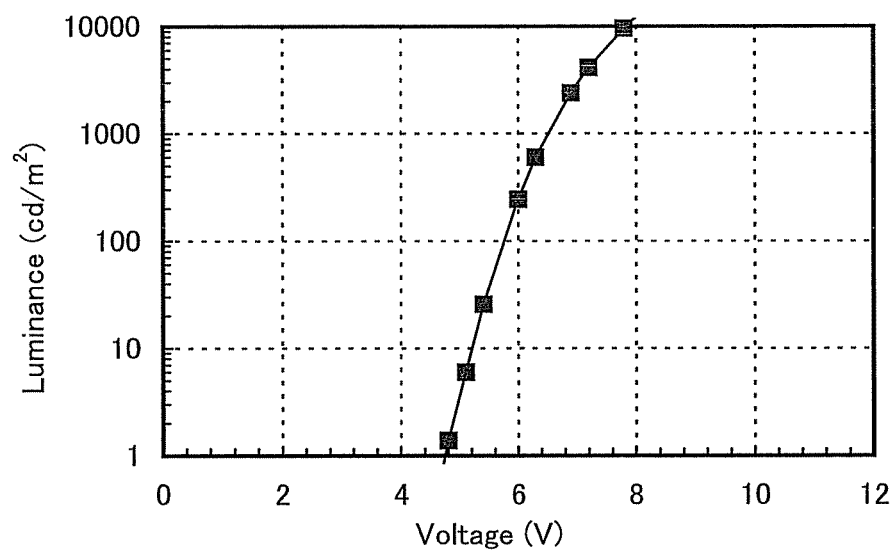
FIG. 17 shows voltage-luminance characteristics of the light-emitting element 1.
Figure 18:
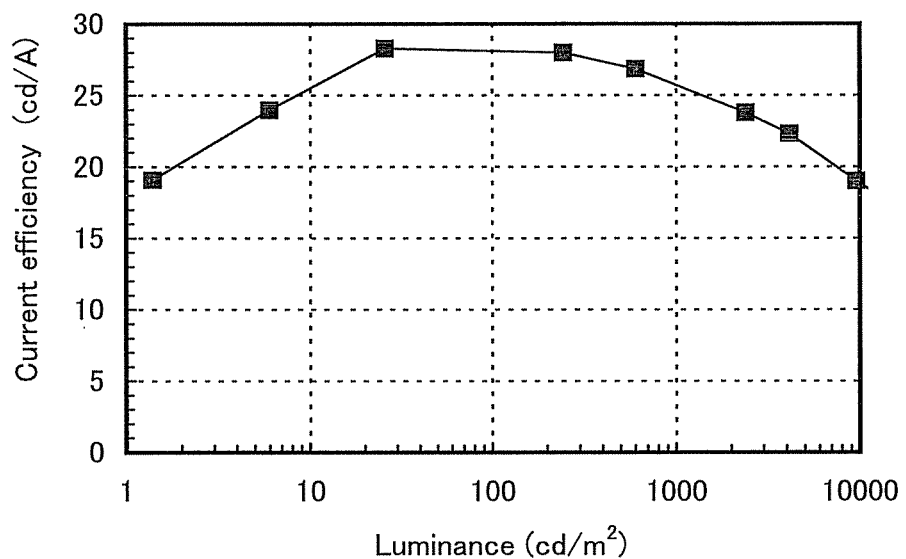
FIG. 18 shows luminance-current efficiency characteristics of the light-emitting element 1.
Figure 19:
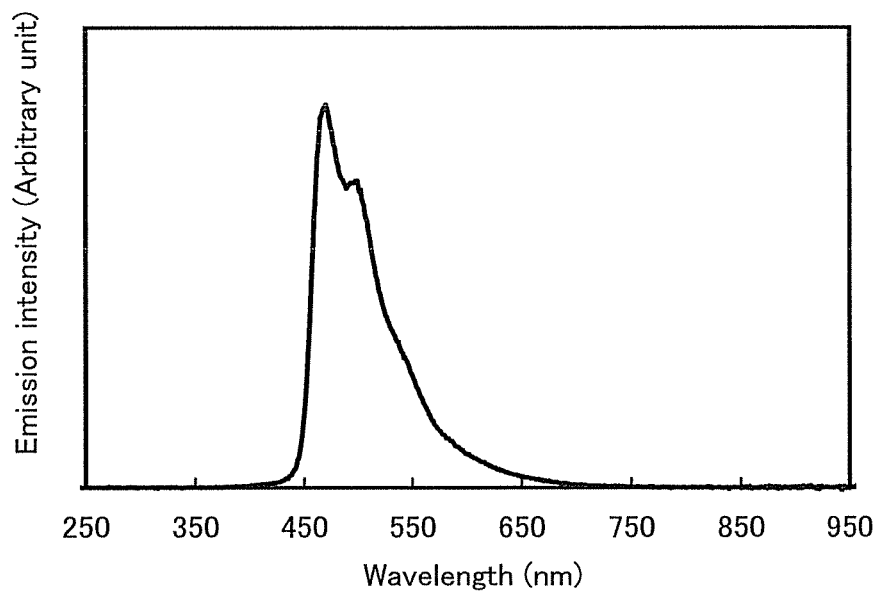
FIG. 19 shows an emission spectrum of the light-emitting element 1.

FIG. 16 shows the current density-luminance characteristics of the light-emitting element 1, FIG. 17 shows the voltage-luminance characteristics thereof, and FIG. 18 shows the luminance-current efficiency characteristics thereof. Further, FIG. 19 shows the emission spectrum of the light-emitting element 1 at a current of 0.1 mA.

Figure 20:
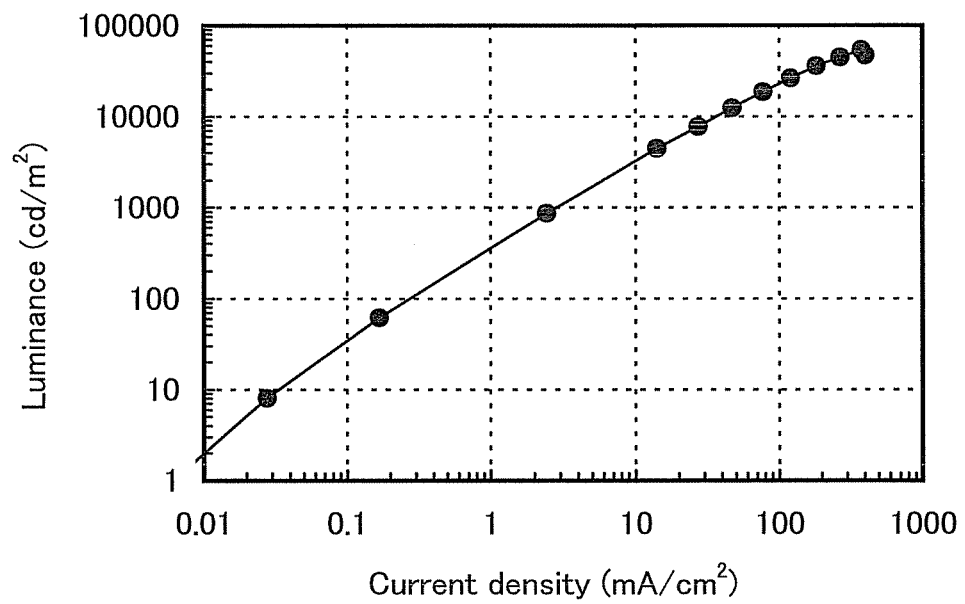
FIG. 20 shows current density-luminance characteristics of a light-emitting element 2.
Figure 21:
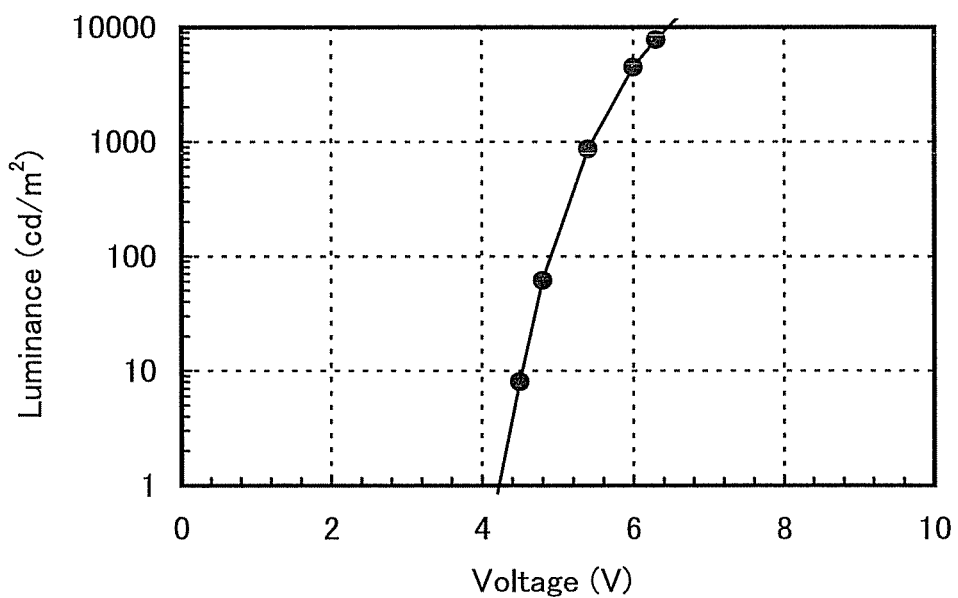
FIG. 21 shows voltage-luminance characteristics of the light-emitting element 2.
Figure 22:
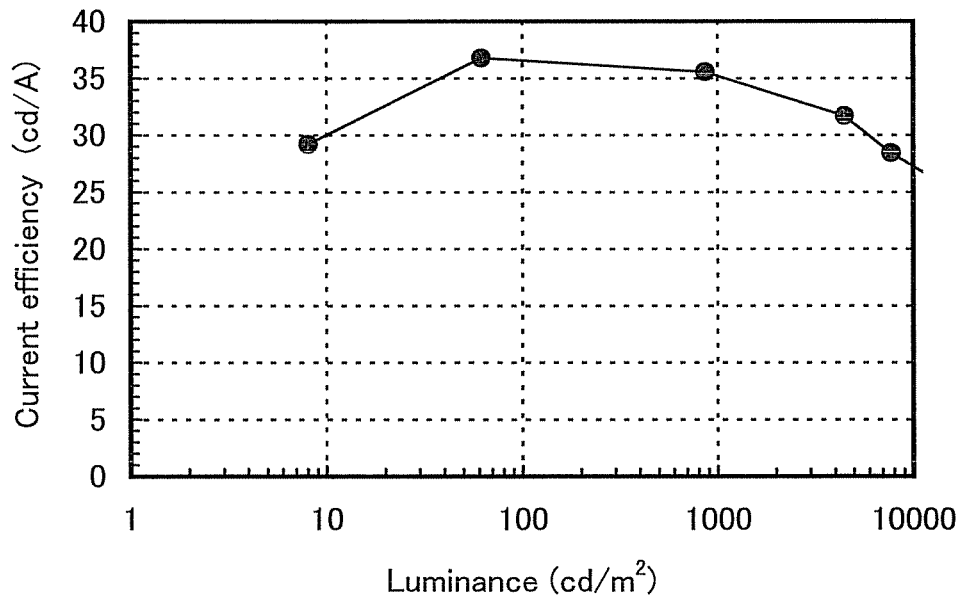
FIG. 22 shows luminance-current efficiency characteristics of the light-emitting element 2.
Figure 23:
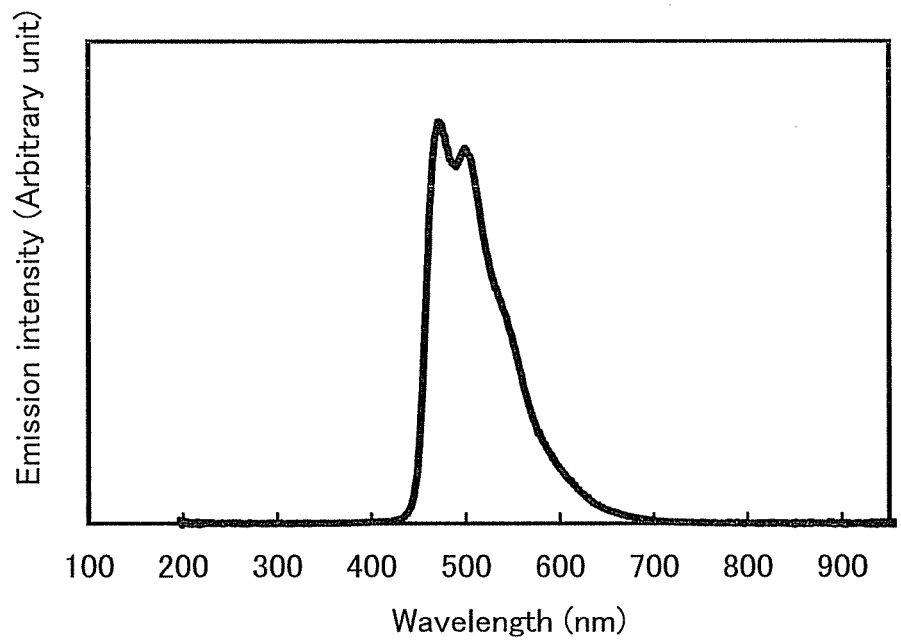
FIG. 23 shows an emission spectrum of the light-emitting element 2.

FIG. 20 shows the current density-luminance characteristics of the light-emitting element 2, FIG. 21 shows the voltage-luminance characteristics thereof, and FIG. 22 shows the luminance-current efficiency characteristics thereof FIG. 23 shows the emission spectrum of the light-emitting element 2 at a current of 0.1 mA.

Table 2 shows the characteristics of the light-emitting element 1 and the light-emitting element 2 at around 1000 cd/m².

The results show that the light-emitting element 1 and the light-emitting element 2 each of which is one embodiment of the present invention are light-emitting elements which can emit blue-green to blue phosphorescence with high emission efficiency.

Figure 24:
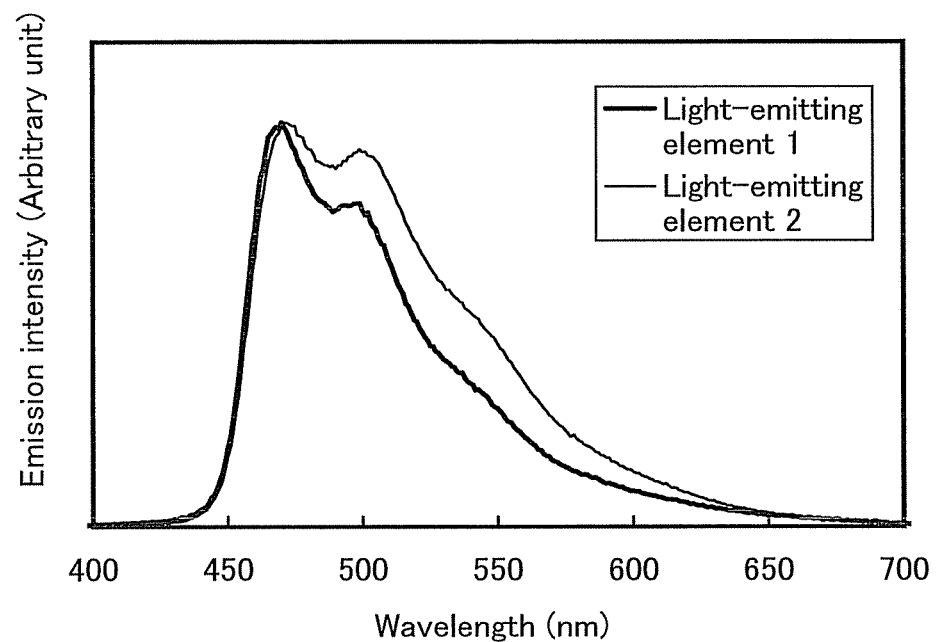
FIG. 24 shows emission spectra of the light-emitting element 1 and the light-emitting element 2.

In FIG. 24, the spectra of both the light-emitting element 1 and the light-emitting element 2 are shown and the wavelength range is different from that in FIG. 23. According to FIG. 24, the light-emitting element 1 which includes Ir(iPrptz-3b)₃ as an emission center substance particularly has a narrow width of the spectrum and low relative intensity on the longer wavelength side, and thus emits favorable blue light. Moreover, according to Table 2, the light-emitting element 1 emits blue light with excellent color purity, which is represented by the CIE chromaticity coordinates (x=0.19, y=0.32) (602 cd/m²).

The above measurement results show that the light-emitting element 1 which includes Ir(iPrptz-3b)₃ as an emission center substance has a sharp spectrum and emits blue phosphorescence with high color purity.

The light-emitting element 2 which includes Ir(iPrptz-4b)₃ as an emission center substance exhibits a particularly excellent quantum efficiency of 15.5%. This shows that the light-emitting element 2 which includes Ir(iPrptz-4b)₃ as an emission center substance emits blue phosphorescence with high emission efficiency.

Reference Example

A method for synthesizing 2-[3-(dibenzothiophen-4-yl)phenyl]-1-phenyl-1H-benzimidazole (abbreviation: mDBTBIm-II) used in Example 4 will be specifically described. Shown below is the structure of mDBTBIm-II.

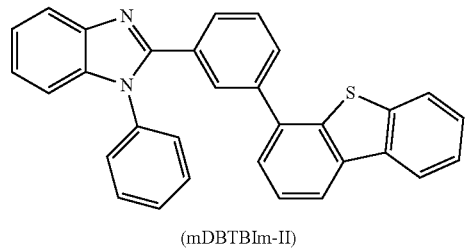 [SMILES: c1ccc(-n2c(-c3cccc(-c4cccc5c4sc4ccccc45)c3)nc3ccccc32)cc1]

(mDBTBIm-II)

Synthesis of 2-[3-(dibenzothiophen-4-yl)phenyl]-1-phenyl-1H-benzimidazole (abbreviation: mDBTBIm-II)

The synthesis scheme of 2-[3-(dibenzothiophen-4-yl)phenyl]-1-phenyl-1H-benzimidazole (abbreviation: mDBTBIm-II) is shown in (f-1).

TABLE 2

| | Voltage (V) | Current (mA) | Chromaticity x | Chromaticity y | Current efficiency (cd/A) | Power efficiency (lm/W) | Quantum efficiency (%) |
|---|---|---|---|---|---|---|---|
| Light-emitting element 1 | 6.3 | 0.09 | 0.19 | 0.32 | 26.9 | 13.4 | 13.3 |
| Light-emitting element 2 | 5.4 | 0.10 | 0.20 | 0.38 | 35.6 | 20.7 | 15.5 |

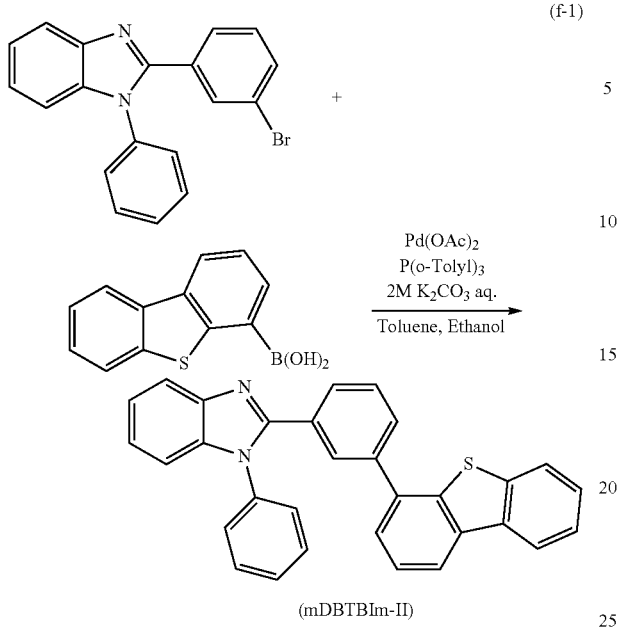

In a 50 mL three-neck flask were put 1.2 g (3.3 mmol) of 2-(3-bromophenyl)-1-phenyl-1H-benzimidazole, 0.8 g (3.3 mmol) of dibenzothiophene-4-boronic acid, and 50 mg (0.2 mmol) of tri(ortho-tolyl)phosphine. The atmosphere in the flask was replaced with nitrogen. To this mixture were added 3.3 mL of a 2.0 mmol/L aqueous solution of potassium carbonate, 12 mL of toluene, and 4 mL of ethanol. This mixture was stirred to be degassed under reduced pressure. To this mixture was added 7.4 mg (33 mmol) of palladium(II) acetate, and the mixture was stirred at 80° C. for 6 hours under a nitrogen stream.

After predetermined time, the aqueous layer of the resulting mixture was extracted with toluene. The resulting solution of the extract and the organic layer were combined, and the mixture was washed with saturated saline and then dried with magnesium sulfate. This mixture was separated by gravity filtration, and the filtrate was concentrated to give an oily substance. This oily substance was purified by silica gel column chromatography. The silica gel column chromatography was carried out using toluene as a developing solvent. The resulting fractions were concentrated to give an oily substance. This oily substance was purified by high performance liquid column chromatography. The high performance liquid column chromatography was performed using chloroform as a developing solvent. The resulting fraction was concentrated to give an oily substance. This oily substance was recrystallized from a mixed solvent of toluene and hexane to give 0.8 g of pale yellow powder, which was the objective substance, in a yield of 51%.

By a train sublimation method, 0.8 g of the resulting pale yellow powder was purified. In the purification, the pale yellow powder was heated at 215° C. under a pressure of 3.0 Pa with a flow rate of argon gas of 5 mL/min. After the purification, 0.6 g of white powder, which was the objective substance, was obtained in a yield of 82%.

A nuclear magnetic resonance (NMR) method identified this compound as 2-[3-(dibenzothiophen-4-yl)phenyl]-1-phenyl-1H-benzimidazole (abbreviation: mDBTBIm-II), which was the objective substance.

The following is $^1$H NMR data of the obtained compound: $^1$H NMR (CDCl$_3$, 300 MHz): δ=7.23-7.60 (m, 13H), 7.71-7.82 (m, 3H), 7.90-7.92 (m, 2H), 8.10-8.17 (m, 2H).

This application is based on Japanese Patent Application serial no. 2011-081583 filed with the Japan Patent Office on Apr. 1, 2011, the entire contents of which are hereby incorporated by reference.

What is claimed is:

1. An organometallic complex comprising a structure represented by General Formula (G1):

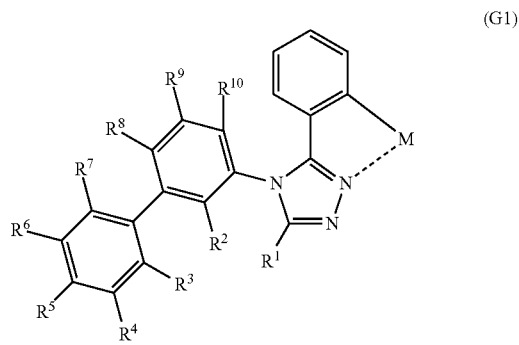

wherein $R^1$ represents an alkyl group having 1 to 4 carbon atoms, wherein $R^2$ to $R^{10}$ each represents hydrogen or an alkyl group having 1 to 4 carbon atoms, and wherein M represents a Group 9 element or a Group 10 element.

2. The organometallic complex according to claim 1, wherein the organometallic complex is represented by General Formula (G3):

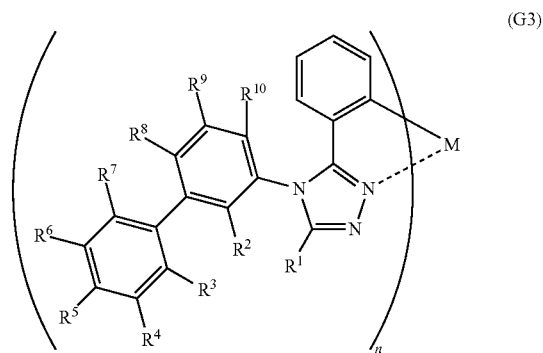

wherein $R^1$ represents an alkyl group having 1 to 4 carbon atoms, wherein $R^2$ to $R^{10}$ each represents hydrogen or an alkyl group having 1 to 4 carbon atoms, wherein M represents a Group 9 element or a Group 10 element, and wherein when M is a Group 9 element, n is 3, and when M is a Group 10 element, n is 2.

3. The organometallic complex according to claim 1, wherein the organometallic complex is represented by Structural Formula (1):

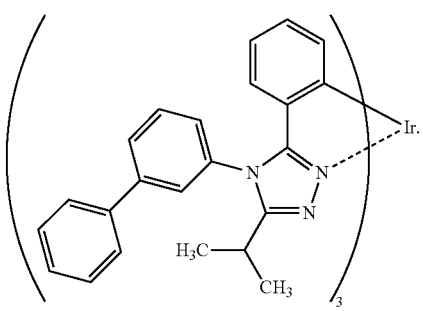

(1)

4. A light-emitting element comprising, between a pair of electrodes, a layer comprising the organometallic complex according to claim 1.

5. The light-emitting element according to claim 4, wherein the layer comprising the organometallic complex is a light-emitting layer.

6. A display device comprising the light-emitting element according to claim 4 in a pixel portion.

7. An electronic device comprising the display device according to claim 6.

8. A lighting device comprising the light-emitting element according to claim 4.

9. A light-emitting element comprising a first light-emitting unit and a second light-emitting unit between a pair of electrodes,
  wherein the first light-emitting unit comprises the organometallic complex according to claim 1, and
  wherein the second light-emitting unit comprises a material emitting light with a wavelength longer than a wavelength of light emitted from the organometallic complex.

10. A light-emitting element comprising a first light-emitting unit, a second light-emitting unit, and a third light-emitting unit between a pair of electrodes,
  wherein the first light-emitting unit comprises the organometallic complex according to claim 1,
  wherein the second light-emitting unit comprises a first light-emitting material emitting light with a wavelength longer than a wavelength of light emitted from the organometallic complex, and
  wherein the third light-emitting unit comprises a second light-emitting material emitting light with a wavelength longer than the wavelength of light emitted from the organometallic complex and shorter than a wavelength of light emitted from the first light-emitting material.

11. An organometallic complex comprising a structure represented by General Formula (G2):

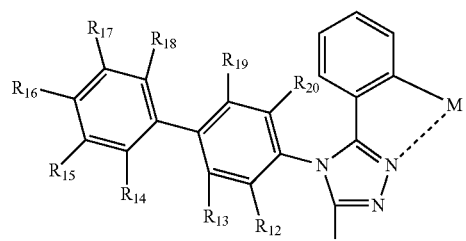

(G2)

wherein $R^{11}$ represents an alkyl group having 1 to 4 carbon atoms, wherein $R^{12}$ to $R^{20}$ each represents hydrogen or an alkyl group having 1 to 4 carbon atoms, and wherein M represents a Group 9 element or a Group 10 element.

12. The organometallic complex according to claim 11, wherein the organometallic complex is represented by General Formula (G4):

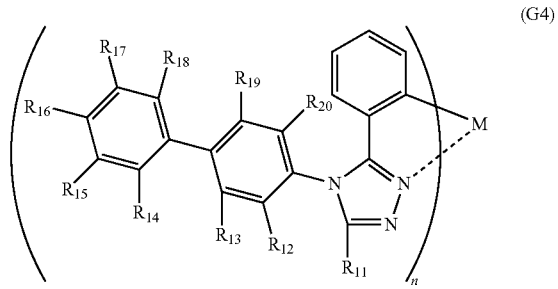

(G4)

wherein $R^{11}$ represents an alkyl group having 1 to 4 carbon atoms, wherein $R^{12}$ to $R^{20}$ each represents hydrogen or an alkyl group having 1 to 4 carbon atoms, wherein M represents a Group 9 element or a Group 10 element, and wherein when M is a Group 9 element, n is 3, and when M is a Group 10 element, n is 2.

13. The organometallic complex according to claim 11, wherein the organometallic complex is represented by Structural Formula (2):

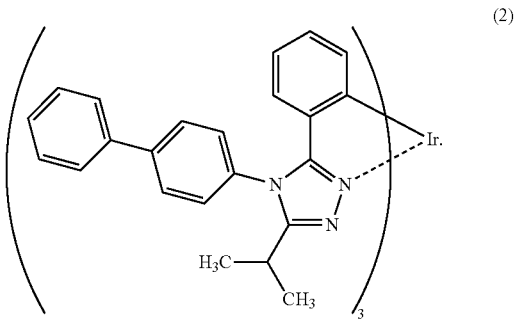

(2)

14. An organometallic complex comprising a structure represented by General Formula (G2):

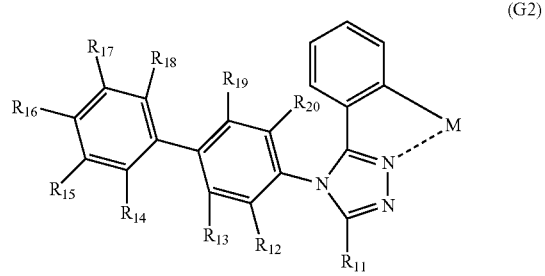

(G2)

wherein $R^{11}$ represents an alkyl group having 1 to 4 carbon atoms, wherein $R^{12}$ and $R^{15}$ to $R^{20}$ each represents hydrogen or an alkyl group having 1 to 4 carbon atoms, wherein $R^{13}$ and $R^{14}$ together are a methylene group which forms a ring, the methylene group unsubstituted or substituted with two alkyl groups each having 1 to 3 carbon atoms, and wherein M represents a Group 9 element or a Group 10 element.

15. The organometallic complex according to claim 14, wherein the organometallic complex is represented by Structural Formula (3):

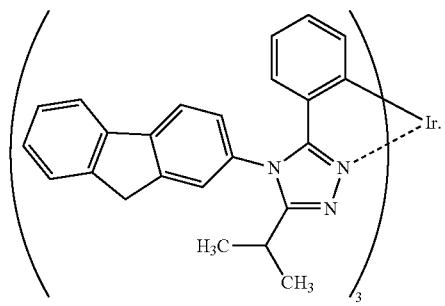

(3)

16. A light-emitting element comprising, between a pair of electrodes, a layer comprising the organometallic complex according to claim 11.

17. The light-emitting element according to claim 16, wherein the layer comprising the organometallic complex is a light-emitting layer.

18. A display device comprising the light-emitting element according to claim 16 in a pixel portion.

19. An electronic device comprising the display device according to claim 18.

20. A lighting device comprising the light-emitting element according to claim 16.

21. A light-emitting element comprising a first light-emitting unit and a second light-emitting unit between a pair of electrodes,
wherein the first light-emitting unit comprises the organometallic complex according to claim 11, and
wherein the second light-emitting unit comprises a material emitting light with a wavelength longer than a wavelength of light emitted from the organometallic complex.

22. A light-emitting element comprising a first light-emitting unit, a second light-emitting unit, and a third light-emitting unit between a pair of electrodes,
wherein the first light-emitting unit comprises the organometallic complex according to claim 11,
wherein the second light-emitting unit comprises a first light-emitting material emitting light with a wavelength longer than a wavelength of light emitted from the organometallic complex, and
wherein the third light-emitting unit comprises a second light-emitting material emitting light with a wavelength longer than the wavelength of light emitted from the organometallic complex and shorter than a wavelength of light emitted from the first light-emitting material.

* * * * *

UNITED STATES PATENT AND TRADEMARK OFFICE
CERTIFICATE OF CORRECTION

PATENT NO. : 9,155,158 B2
APPLICATION NO. : 13/432253
DATED : October 6, 2015
INVENTOR(S) : Hideko Inoue et al.

Page 1 of 3

It is certified that error appears in the above-identified patent and that said Letters Patent is hereby corrected as shown below:

In the Title Page:

Item (57) Abstract, Line 8; Change "N is 2." to --n is 2.--.

Item (57) Abstract, Line 13; Change "N is 2." to --n is 2.--.

In the Specification:

Column 11, Lines 54 to 67, structure formula (109);

Change "
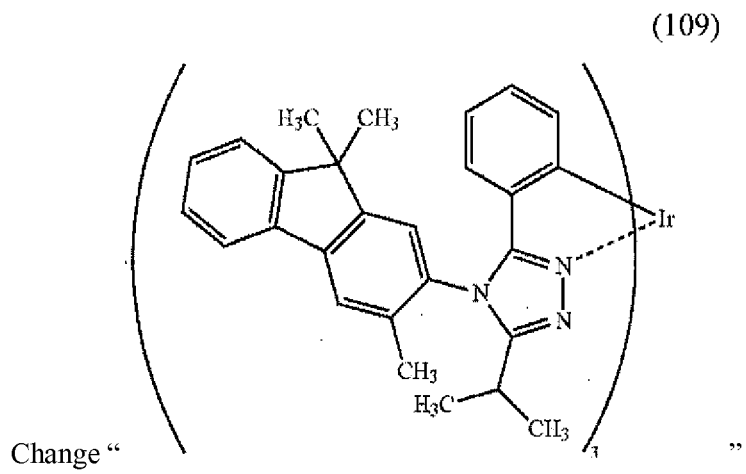
"

Signed and Sealed this
Fifth Day of April, 2016

Michelle K. Lee
*Director of the United States Patent and Trademark Office*

(109)
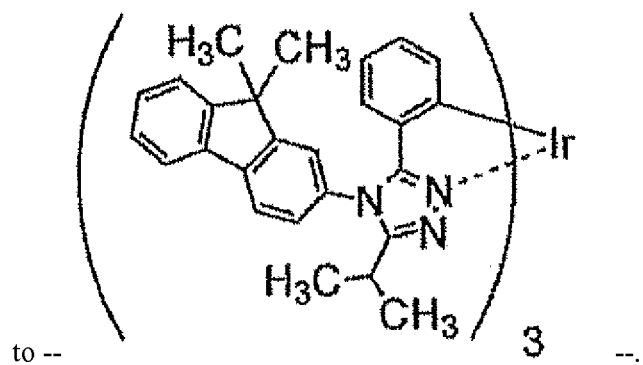
to -- --.
Column 16, Line 8; Change "manner as" to --manner: as--.
Column 19, Line 46; Change "hydroxyphenypbenzothiazolato]" to --hydroxyphenyl)benzothiazolato]"--.
Column 27, Line 39; Change "aim 9403," to --arm 9403,--.
Column 33, Line 57 to 67, synthesis scheme (a-5);
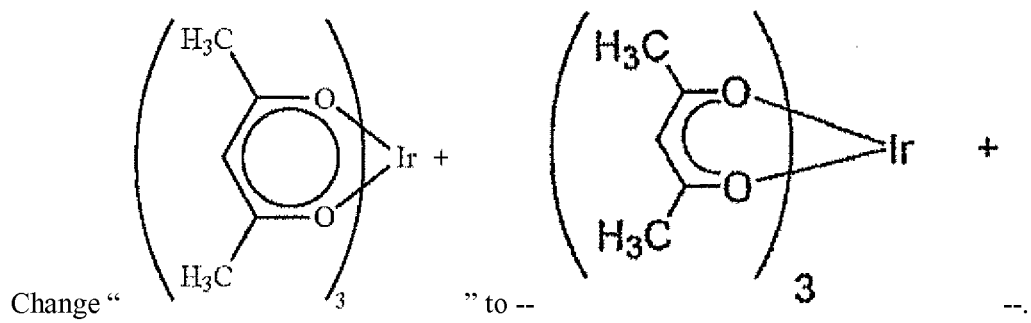
Change " (a-5) " to -- (a-5) --.
Column 34, Line 33; Change "($^1$H-NMIR)" to --($^1$H-NMR)--.
Column 34, Line 52; Change "(F5920," to --(FS920,--.
Column 39, Lines 1 to 9, reaction scheme (b-6);
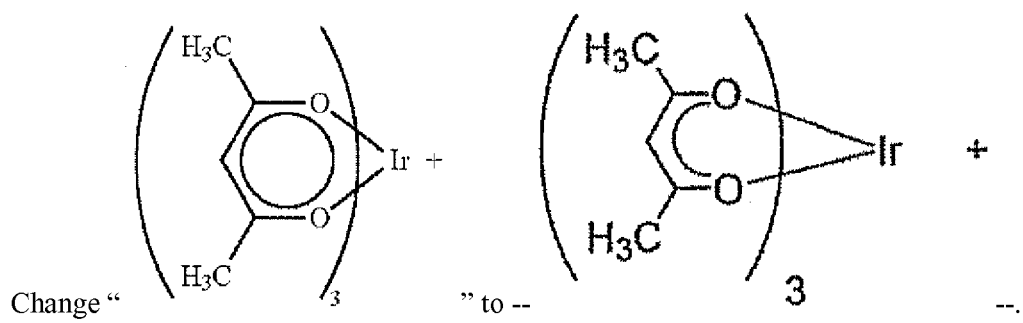
Change " (b-6) " to -- (b-6) --.

CERTIFICATE OF CORRECTION (continued)
U.S. Pat. No. 9,155,158 B2

Column 42, Lines 58 to 66, synthesis scheme (c-4);

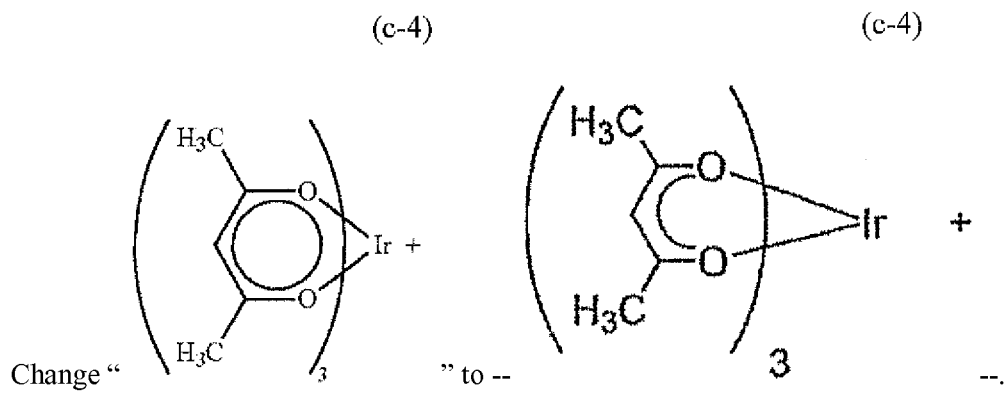

Column 43, Line 31; Change "$^1$NMR" to --$^1$H-NMR--.

Column 47, Line 51; Change "thereof FIG. 23" to --thereof. FIG. 23--.

Column 50, Line 2; Change "5=7.23-7.60" to --δ=7.23-7.60--.